United States Patent
Grenier et al.

(10) Patent No.: US 7,425,340 B2
(45) Date of Patent: Sep. 16, 2008

(54) PERMEATION ENHANCING COMPOSITIONS FOR ANTICHOLINERGIC AGENTS

(75) Inventors: Arnaud Grenier, Steinbrunn-le-Haut (FR); Dario Norberto R. Carrara, Oberwil (CH); Celine Besse, Huningue (FR)

(73) Assignee: Antares Pharma IPL AG, Zug (CH)

( * ) Notice: Subject to any disclaimer, the term of this patent is extended or adjusted under 35 U.S.C. 154(b) by 344 days.

(21) Appl. No.: 11/120,306

(22) Filed: May 2, 2005

(65) Prior Publication Data

US 2005/0287194 A1    Dec. 29, 2005

Related U.S. Application Data

(60) Provisional application No. 60/568,983, filed on May 7, 2004.

(51) Int. Cl.
  A61K 31/24    (2006.01)
  A61K 9/00    (2006.01)
(52) U.S. Cl. .................... 424/400; 514/818; 514/821
(58) Field of Classification Search .............. 424/59, 424/60, 400, 449; 514/534
See application file for complete search history.

(56) References Cited

U.S. PATENT DOCUMENTS

| | | | |
|---|---|---|---|
| 4,082,881 A | 4/1978 | Chen et al. ............... 514/39 |
| 4,315,925 A | 2/1982 | Hussain et al. .............. 514/177 |
| 4,383,993 A | 5/1983 | Hussain et al. .............. 514/177 |
| 4,390,532 A | 6/1983 | Stuttgen et al. .............. 514/56 |
| 4,537,776 A | 8/1985 | Cooper ..................... 514/424 |
| 4,597,961 A | 7/1986 | Etscorn ..................... 424/448 |
| 4,704,406 A | 11/1987 | Stanislaus et al. .......... 514/570 |
| 4,764,381 A | 8/1988 | Bodor et al. ................. 424/449 |
| 4,832,953 A | 5/1989 | Campbell et al. ............ 424/448 |
| 4,863,970 A | 9/1989 | Patel et al. .................. 514/784 |
| 4,883,660 A | 11/1989 | Blackman et al. ............. 424/78 |
| 4,952,560 A | 8/1990 | Kigasawa et al. ............... 514/2 |
| 4,956,171 A | 9/1990 | Chang ........................ 424/449 |
| 4,973,468 A | 11/1990 | Chiang et al. ............... 424/449 |
| 5,041,439 A | 8/1991 | Kasting et al. ............ 514/227.2 |
| 5,053,227 A | 10/1991 | Chiang et al. ............... 424/448 |
| 5,059,426 A | 10/1991 | Chiang et al. ............... 424/449 |
| 5,071,657 A | 12/1991 | Oloff et al. .................. 424/486 |
| 5,128,138 A | 7/1992 | Blank ........................ 424/449 |

(Continued)

FOREIGN PATENT DOCUMENTS

EP    0 249 397 A2    12/1987

(Continued)

OTHER PUBLICATIONS

English Abstract NLM2807923 XP-002337932, "Promoting Penetration Of Locally Applied Substances By Urea".

(Continued)

*Primary Examiner*—Michael G. Hartley
*Assistant Examiner*—Jagadishwar R Samala
(74) *Attorney, Agent, or Firm*—Winston & Strawn LLP

(57) ABSTRACT

A transdermal or topical composition including anticholinergic agents, such as oxybutynin, a urea-containing compound and a carrier system. A method is disclosed for treating a subject for urinary incontinence while reducing the incidences of peak concentrations of drug and undesirable side effects.

20 Claims, 16 Drawing Sheets

U.S. PATENT DOCUMENTS

| | | | | |
|---|---|---|---|---|
| 5,164,190 | A | 11/1992 | Patel et al. | 424/448 |
| 5,178,879 | A | 1/1993 | Adekunle et al. | 424/484 |
| 5,230,896 | A | 7/1993 | Yeh et al. | 424/443 |
| 5,232,703 | A | 8/1993 | Blank | 424/449 |
| 5,238,933 | A | 8/1993 | Catz et al. | 514/236.2 |
| 5,278,176 | A | 1/1994 | Lin | 514/343 |
| 5,352,457 | A | 10/1994 | Jenkins | 424/448 |
| 5,371,005 | A | 12/1994 | Fujishiro et al. | 435/190 |
| 5,453,279 | A | 9/1995 | Lee et al. | 424/448 |
| 5,527,832 | A | 6/1996 | Chi et al. | 514/772.4 |
| 5,532,278 | A | 7/1996 | Aberg et al. | 514/617 |
| 5,580,574 | A | 12/1996 | Behl et al. | 424/449 |
| 5,601,839 | A | 2/1997 | Quan et al. | 424/448 |
| 5,602,017 | A | 2/1997 | Fujishiro et al. | 435/190 |
| 5,603,947 | A | 2/1997 | Wong et al. | 424/448 |
| 5,629,021 | A | 5/1997 | Wright | 424/489 |
| 5,633,008 | A | 5/1997 | Osborne et al. | 424/448 |
| 5,658,587 | A | 8/1997 | Santus et al. | 424/448 |
| 5,660,839 | A | 8/1997 | Allec et al. | 424/401 |
| 5,662,890 | A | 9/1997 | Punto et al. | 424/59 |
| 5,665,560 | A | 9/1997 | Fujishiro et al. | 435/11 |
| 5,677,346 | A | 10/1997 | Aberg et al. | 51/617 |
| 5,716,638 | A | 2/1998 | Touitou | 424/450 |
| 5,719,197 | A | 2/1998 | Kanios et al. | 514/772.6 |
| 5,731,303 | A | 3/1998 | Hsieh | 514/183 |
| 5,736,577 | A | 4/1998 | Aberg et al. | 514/617 |
| 5,783,207 | A | 7/1998 | Stanley et al. | 424/449 |
| 5,785,991 | A | 7/1998 | Burkoth et al. | 424/448 |
| 5,798,242 | A | 8/1998 | Fujishiro et al. | 435/190 |
| 5,814,659 | A | 9/1998 | Elden | 514/452 |
| 5,831,035 | A | 11/1998 | Timms | 530/389.1 |
| 5,834,010 | A | 11/1998 | Quan et al. | 424/448 |
| 5,855,905 | A | 1/1999 | Oettel et al. | 424/426 |
| 5,855,920 | A | 1/1999 | Chein | 424/568 |
| 5,891,462 | A | 4/1999 | Carrara | 424/449 |
| 5,900,250 | A | 5/1999 | Lee et al. | 424/448 |
| 5,904,931 | A | 5/1999 | Lipp et al. | 424/449 |
| 5,922,349 | A | 7/1999 | Elliesen et al. | 424/449 |
| 5,932,243 | A | 8/1999 | Fricker et al. | 424/450 |
| 5,935,604 | A | 8/1999 | Illum | 424/501 |
| 5,968,919 | A | 10/1999 | Samour et al. | 514/177 |
| 6,008,192 | A | 12/1999 | Al-Razzak et al. | 514/11 |
| 6,034,079 | A | 3/2000 | Sandberg et al. | 514/225.8 |
| 6,060,077 | A | 5/2000 | Meignant | 424/434 |
| 6,096,733 | A | 8/2000 | Lubkin | 514/182 |
| 6,123,961 | A | 9/2000 | Aberg | 424/468 |
| 6,124,355 | A | 9/2000 | Guittard et al. | 514/534 |
| 6,153,216 | A | 11/2000 | Cordes et al. | 424/449 |
| 6,165,497 | A | 12/2000 | Osborne et al. | 424/448 |
| 6,166,044 | A | 12/2000 | Sandborn et al. | 514/343 |
| 6,180,803 | B1 | 1/2001 | Piasco et al. | 552/510 |
| 6,267,985 | B1 | 7/2001 | Chen et al. | 424/451 |
| 6,284,234 | B1 | 9/2001 | Niemiec et al. | 424/78.07 |
| 6,299,900 | B1 | 10/2001 | Reed et al. | 424/449 |
| 6,309,843 | B1 | 10/2001 | Timms | 435/7.1 |
| 6,319,913 | B1 | 11/2001 | Mak et al. | 514/179 |
| 6,383,471 | B1 | 5/2002 | Chen et al. | 424/45 |
| 6,417,205 | B1 | 7/2002 | Cooke et al. | 514/343 |
| 6,426,078 | B1 | 7/2002 | Bauer et al. | 424/401 |
| 6,432,446 | B2 | 8/2002 | Aberg | 424/468 |
| 6,440,454 | B1 | 8/2002 | Santoro et al. | 424/449 |
| 6,444,234 | B1 | 9/2002 | Kirby et al. | 424/725 |
| 6,465,005 | B1 | 10/2002 | Biali et al. | 424/449 |
| 6,476,012 | B2 | 11/2002 | Hochberg | 514/182 |
| 6,479,076 | B2 | 11/2002 | Blank | 424/484 |
| 6,497,897 | B2 | 12/2002 | Hidaka et al. | 424/449 |
| 6,503,894 | B1 | 1/2003 | Dudley et al. | 514/178 |
| 6,545,046 | B2 | 4/2003 | Sherratt et al. | 514/534 |
| 6,586,000 | B2 | 7/2003 | Luo et al. | 424/449 |
| 6,596,740 | B2 | 7/2003 | Jones | 514/343 |
| 6,743,441 | B2 | 6/2004 | Sanders et al. | 424/448 |
| 6,818,226 | B2 | 11/2004 | Reed et al. | 424/449 |
| 6,828,336 | B2 | 12/2004 | Walling | 514/343 |
| 6,929,801 | B2 | 8/2005 | Klose et al. | 424/448 |
| 2001/0023261 | A1 | 9/2001 | Ryoo | 514/772 |
| 2001/0031787 | A1* | 10/2001 | Hsu et al. | 514/534 |
| 2001/0033870 | A1 | 10/2001 | Luo et al. | 424/688 |
| 2001/0038855 | A1 | 11/2001 | Desjardin et al. | 424/468 |
| 2002/0147236 | A1 | 10/2002 | Sanders et al. | 514/540 |
| 2002/0183296 | A1 | 12/2002 | Dudley et al. | 514/177 |
| 2003/0022877 | A1 | 1/2003 | Dudley | 514/177 |
| 2003/0050292 | A1 | 3/2003 | Dudley et al. | 514/177 |
| 2003/0095926 | A1 | 5/2003 | Dugger, III | 424/43 |
| 2003/0139384 | A1 | 7/2003 | Dudley | 514/177 |
| 2003/0143278 | A1 | 7/2003 | DiPiano et al. | 424/489 |
| 2003/0147926 | A1* | 8/2003 | Ebert et al. | 424/400 |
| 2003/0175329 | A1 | 9/2003 | Azarnoff et al. | 424/449 |
| 2003/0181430 | A1 | 9/2003 | Gray et al. | 514/170 |
| 2003/0199426 | A1 | 10/2003 | Carrara et al. | 514/2 |
| 2003/0222105 | A1 | 12/2003 | Lee et al. | 222/382 |
| 2003/0232072 | A1 | 12/2003 | Dudley et al. | 424/449 |
| 2004/0002482 | A1 | 1/2004 | Dudley et al. | 514/169 |
| 2004/0139990 | A1 | 7/2004 | Wachter et al. | 134/25.4 |
| 2004/0198706 | A1 | 10/2004 | Carrara et al. | 514/169 |
| 2004/0213744 | A1 | 10/2004 | Lulla et al. | 424/45 |
| 2004/0219197 | A1 | 11/2004 | Carrara et al. | 424/449 |

FOREIGN PATENT DOCUMENTS

| | | |
|---|---|---|
| EP | 0 250 125 B1 | 12/1987 |
| EP | 0 261 429 A1 | 3/1988 |
| EP | 0 267 617 A1 | 5/1988 |
| EP | 0 271 983 A1 | 6/1988 |
| EP | 0 279 977 A2 | 8/1988 |
| EP | 0 325 613 B1 | 6/1989 |
| EP | 0 367 431 A1 | 5/1990 |
| EP | 0 409 383 B1 | 1/1991 |
| EP | 0 435 200 B1 | 7/1991 |
| EP | 0 491 803 B1 | 7/1992 |
| EP | 0 526 561 B1 | 2/1993 |
| EP | 0 643 963 B1 | 3/1995 |
| EP | 0 655 900 B1 | 6/1995 |
| EP | 0 672 422 A1 | 9/1995 |
| EP | 0 719 538 B1 | 7/1996 |
| EP | 0 785 211 A1 | 7/1997 |
| EP | 0 785 212 A1 | 7/1997 |
| EP | 0 802 782 B1 | 10/1997 |
| EP | 0 804 926 B1 | 11/1997 |
| EP | 0 811 381 A1 | 12/1997 |
| EP | 0 814 776 B1 | 1/1998 |
| EP | 0 859 793 B1 | 8/1998 |
| EP | 0 868 187 | 10/1998 |
| EP | 1 089 722 B1 | 4/2001 |
| EP | 1 323 430 A2 | 7/2003 |
| EP | 1 323 431 A2 | 7/2003 |
| EP | 1 325 752 A2 | 7/2003 |
| FR | 2 518 879 A1 | 7/1983 |
| FR | 2 776 191 A1 | 9/1999 |
| JP | 9-176049 A | 7/1997 |
| WO | WO 90/11064 A1 | 10/1990 |
| WO | WO 92/08730 A1 | 5/1992 |
| WO | WO 94/06437 A1 | 3/1994 |
| WO | WO 95/18603 A1 | 7/1995 |
| WO | WO 95/29678 A1 | 11/1995 |
| WO | WO 97/03676 A1 | 2/1997 |
| WO | WO 97/29735 A1 | 8/1997 |
| WO | WO 97/34607 A1 | 9/1997 |
| WO | WO 98/17316 A1 | 4/1998 |
| WO | WO 98/37879 A1 | 9/1998 |
| WO | WO 99/20257 A1 | 4/1999 |
| WO | WO 99/24041 A1 | 5/1999 |
| WO | WO 99/48477 A1 | 9/1999 |
| WO | WO 01/80796 A1 | 11/2001 |
| WO | WO 02/11768 | 2/2002 |

| WO | WO 02/17967 A1 | 3/2002 |
| WO | WO 02/22132 A2 | 3/2002 |

OTHER PUBLICATIONS

David W. Osborne et al., XP 002337808, "Skin Penetration Enhancers Cited in the Technical Literature".

A.C. Williams et al., XP 000645464, "Urea Analogues In Propylene Glycol As Penetration Enhancers In Human Skin", International Journal of Pharmaceutics, vol. 36, pp. 43-50 (1989).

Koichi Takahashi et al., "Effect of Vehicles on Diclofenac Permeation across Excised Rat Skin", Biol. Pharm. Bull., vol. 18, No. 4, pp. 571-575 (1995).

Budavari et al., The Merk Index, 1996, Merck Research Laboratories, 12th Edition, pp. 253 and 269.

Kotiyan et al., "Eudragits:Role as crystallization inhibitors in drug-in-adhesive transdermal systems of estradiol," European Journal of Pharmaceutics and Biopharmaceutics 52: 173-180 (2001).

Lipp, "Selection and use of crystallization inhibitors for matrix-type transdermal drug-delivery systems containing sex steroids," J. Pharm. Pharmacol. 50: 1343-1349 (1998).

Moser et al., "Passive skin penetration enhancement and its quantification in vitro," European Journal of Pharmaceutics and Biopharmaceutics 52: 103-112 (2001).

Mura et al., "Evaluation of transcutol as a clonazepam transdermal permeation enhancer from hydrophilic gel formulations," European Journal of Pharmaceutical Sciences 9: 365-372 (2000).

R. Panchagnula et al., "Development and evaluation of an intracutaneous depot formulation of corticosteroids using transcutol as a cosolvent: in-vitro, ex-vivo and in-vivo rat studies," J. Pharm. Pharmacol. 1991, 43: 609-614.

L. Pavliv et al., "Topical formulation development of a novel thymidylate synthase inhibitor for the treatment of psoriasis," International Journal of Pharmaceutics 1994, 105: 227-233.

W.A. Ritschel et al., "In vitro skin penetration of griseofulvin in rat and human skin from an ointment dosage form," Arzneimittelforschung. 1988, 38(11): 1630-1632.

W.A. Ritschel et al., "Use of sorption promoters to increase systemic absorption of coumarin from transdermal drug delivery systems," Arzneimittelforschung. 1988, 38(12): 1774-1777.

W.A. Ritschel et al., "Development of an intracutaneous depot for drugs," Skin Pharmacol. 1991, 4:235-245.

J. Rojas, "Optimization of binary and ternary solvent systems in the percutaneous absorption of morphine base," S.T.P. Pharma Sciences 1991, 1(1): 70-75.

E. Touitou, "Enhanced permeation of theophylline through the skin and its effect on fibroblast proliferation," International Journal of Pharmaceutics 1991, 70: 159-166.

A. Watkinson, "Aspects of the transdermal delivery of prostaglandins," International Journal of Pharmaceutics 1991, 74: 229-236.

M. Yazdanian et al., "The effect of diethylene glycol monoethyl ether as a vehicle for topical delivery of ivermectin," Veterinary Research Communications 1995, 19(4): 309-319.

P. Karande and S. Mitragotri, "High Throughput Screening of Transdermal Formulations," Pharmaceutical Research, 2002, 19(5): 655-660.

US 6,214,374, 04/2001, Schmirier et al. (withdrawn)

* cited by examiner

24-hour *In Vitro* Comparative Permeation Study of Compositions Comprising Oxybutynin and Urea to Compositions Comprising Oxybutynin Without Urea

24-hour In Vitro Comparative Permeation Study Of Compositions Comprising Oxybutynin, A Hydroalcoholic Carrier, And Solvents

Drug Flux Profile of Oxybutynin Compositions

24-hour In Vitro Comparative Permeation Study Of Compositions Comprising Oxybutynin and Complex Hydroalcoholic Carriers

Drug Flux Profile For Compositions Comprising Oxybutynin

Mean Oxybutynin Plasma Concentrations Profiles Obtained From Pharmacokinetic Study

Mean Metabolite Plasma Concentrations Profiles Obtained From Pharmacokinetic Study

Evolution Of Oxybutynin And Its Metabolite During Treatment A Obtained From Pharmacokinetic Study

Evolution Of Oxybutynin And Its Metabolite During Treatment B Obtained From Pharmacokinetic Study

24-hour *In Vitro* Comparative Permeation Study of Compositions Comprising Oxybutynin and Urea to Compositions Comprising Oxybutynin and Lauric Acid and Compositions Comprising Oxybutynin and Isopropyl Myristate

Drug Flux Profile of Oxybutynin Compostions

24-hour *In Vitro* Comparative Permeation Study of Compositions Comprising Oxybutynin and Urea to Compositions Comprising Oxybutynin and Triacetin and Oxybutynin and Glycerol Monooleate Drug Flux Profile of Oxybutynin Compositions Containing either Urea, Triacetin or Glycerol Monooleate

24-hour *In Vitro* Comparative Permeation Study of Compositions Comprising Tolterodine Hydrogen Tartrate and Urea to Compositions Comprising Tolterodine Hydrogen Tartrate Without Urea

24-hour *In Vitro* Comparative Permeation Study of Compositions Comprising Tolterodine Hydrogen Tartrate and Dimethyl Urea to Compositions Comprising Tolterodine Hydrogen Tartrate Without Dimethyl Urea Drug Flux Profile of Tolterodine Compositions

PERMEATION ENHANCING COMPOSITIONS FOR ANTICHOLINERGIC AGENTS

CROSS-REFERENCE

This application claims the benefit of U.S. Provisional Patent Application Ser. No. 60/568,983, filed May 7, 2004, the contents of which are incorporated herein by reference thereto.

TECHNICAL FIELD

This invention relates generally to compositions comprising anticholinergic or antispasmodic agents, and more particularly relates compositions that enhance the permeability of skin or mucosal tissue to topically or transdermally applied anticholinergic or antispasmodic agents, and in particular oxybutynin. The invention also relates to methods for treating overactive bladder and urinary incontinence by the administration of the topical or transdermal composition.

BACKGROUND OF THE INVENTION

It is currently known that topical or transdermal delivery systems for the administration of drugs offer several advantages over oral delivery of the same drugs. Generally, the advantages of topical or transdermal delivery of drugs relate to pharmacokinetics. More specifically, one common problem associated with the oral delivery of drugs is the occurrence of peaks in serum levels of the drug, which is followed by a drop in serum levels of the drug due to its elimination and possible metabolism. Thus, the serum level concentrations of orally administered drugs have peaks and valleys after ingestion. These highs and lows in serum level concentrations of drug often lead to undesirable side effects.

In contrast, topical and transdermal delivery of drugs provides a relatively slow and steady delivery of the drug. Accordingly, unlike orally administered drugs, the serum concentrations of topically or transdermally delivered drugs are substantially sustained and do not have the peaks associated with oral delivery.

The sustained serum concentrations associated with topical or transdermal drug delivery avoids the systemic side effects of oral administration of drugs. Specifically, first pass metabolism of the drug by the liver is circumvented by utilizing transdermal or topical delivery vehicles for the administration of drugs.

The advantages of topical or transdermal drug delivery vehicles as compared to oral drug delivery is generally well-known for various drugs. For instance, Powers et al. demonstrated advantages of transdermal estradiol over oral estradiol. See, Powers M S, Schenkel L, Darkey P E, Good W R, Balestra J C, Place V A; "Pharmacokinetics and pharmacodynamics of transdermal dosage forms of 17β-estradiol: Comparison with conventional oral estrogens for hormone replacement," Am. J. Obstet. Gynecol., 1985; 152:1099. Van Seventer et al reported that patient assessment favored transdermal fentanyl treatment over sustained release morphine in terms of a significantly lower rate of troublesome side-effects and less interruption of daily activities. See, Van Seventer R, Smit J M, Schipper R M, Wicks M A, Zuurmond W W, "Comparison of TTS-fentanyl with sustained-release oral morphine in the treatment of patients not using opioids for mild-to-moderate pain."; Curr Med Res Opin. 2003;19(6): 457-69.

Additionally, Heyneman et al. reported that topically applied nonsteroidal anti-inflammatory drugs (NSAIDs) have a superior safety profile to oral formulations. Also reported was that adverse effects, secondary to topical NSAID application, occur in approximately 10 to 15% of patients and are primarily cutaneous in nature (rash and pruritus at site of application); gastrointestinal adverse drug reactions are rare with topically applied NSAIDs, compared with a 15% incidence reported for oral NSAIDs. See, Heyneman C A, Lawless-Liday C, Wall G C, "*Oral versus topical NSAIDs in rheumatic diseases: a comparison*", Drugs. September 2000;60(3):555-74.

Barrett et al. found that the plasma concentrations of selegiline after transdermal application was more than 50-fold greater than that obtained with oral selegiline. This increase in systemic plasma concentrations of selegiline at the expense of metabolites formation that is reduced to less than 70% of that obtained orally is hypothesized to be of therapeutic value in patients with a variety of neurodegenerative and psychiatric disorders. See, Barrett J S, Hochadel T J, Morales R J, Rohatagi S, DeWitt K E, Watson S K, DiSanto A R; "Pharmacokinetics and Safety of a Selegiline Transdermal System Relative to Single-Dose Oral Administration in the Elderly."; Am J Ther. October 1996;3(10):688-698.

Likewise, it is also generally known that there exists a significant decrease in adverse effects associated with the transdermal delivery of oxybutynin. Oral oxybutynin has been indicated for the relief of symptoms of bladder instability associated with voiding in patients with uninhibited neurogenic or reflex neurogenic bladder, i.e., urgency, frequency, urinary leakage, urge incontinence, and dysuria.

Oxybutynin has been found to have a direct antispasmodic effect on smooth muscle and inhibits the muscarinic action of acetylcholine on smooth muscle, but exhibits only one-fifth of the anticholinergic activity of atropine detrusor muscle (effect observed in rabbits), and four to ten times its antispasmodic activity. Oxybutynin has not been found to possess blocking effects at skeletal neuromuscular junctions or autonomic ganglia (antinicotinic effects).

Moreover, oxybutynin has been found to relax bladder smooth muscle. In patients with conditions characterized by involuntary bladder contractions, cystometric studies have demonstrated that oxybutynin increases bladder (vesical) capacity, diminishes the frequency of uninhibited contractions of the detrusor muscle, and delays the initial desire to void. Oxybutynin thus decreases urgency and the frequency of both incontinent episodes and voluntary urination. It has also been reported that antimuscarinic activity resides predominantly in the R-isomer.

Adverse reactions associated with oxybutynin therapy, however, may include cardiovascular manifestations such as palpitations, tachycardia or vasodilatation; dermatologic manifestations such as decreased sweating, rash; gastrointestinal/genitourinary manifestations such as constipation, decreased gastrointestinal motility, dry mouth, nausea, urinary hesitance and retention; nervous system manifestations such as asthenia, dizziness, drowsiness, hallucinations, insomnia, restlessness; opthalmic manifestations such as amblyopia, cycloplegia, decreased lacrimation, mydriasis. Most common side effects associated with oral oxybutynin encompasses dry mouth, dizziness, blurred vision, and constipation. These adverse experiences may be uncomfortable enough to persuade the patient to discontinue treatment.

In a study which compared transdermal delivery and oral delivery of oxybutynin, a substantially lower fluctuation in oxybutynin and its metabolite N-desethyloxybutynin plasma concentrations was demonstrated with the transdermally administered oxybutynin. Additionally, reduced N-desethyloxybutynin formation, and greater saliva production during the dosing period was reported compared with oral oxybutynin administration. Moreover, lower incidences of dry mouth in patients with overactive bladder were reported. See, Appel R A, Chancellor M B, Zobrist R H, Thomas H, Sanders S W, "Pharmacokinetics, Metabolism, and Saliva Output during Transdermal and Extended-Release Oral Oxybutynin Administration in Healthy Subjects", Mayo Clin. Proc. 2003; 78: 696-702.

Moreover, Dmochowsky et al. confirmed the improvement of overactive bladder symptoms and quality of life (dry mouth incidence reduction) in patients treated with transdermal oxybutynin compared to oral oxybutynin therapy. See, Dmochowski R R, Davila G W, Zinner N R, Gittelman M C, Saltzstein D R, Lyttle S, Sanders S W; For The Transdermal Oxybutynin Study Group.; "*Efficacy and safety of transdermal oxybutynin in patients with urge and mixed urinary incontinence*", The Journal of Urology, Vol. 168, 580-586, Aug. 2002. Thus, it can be easily seen that transdermal delivery of oxybutynin has been shown to be more advantageous, as well as preferred over oral delivery of oxybutynin.

As known in the art, the transdermal administration of drugs has certain drawbacks associated with drug penetration across the dermal barrier. Skin is a structurally complex multilayered organ with a total thickness of 2-3 mm. Thus, penetration of drugs to skin is only efficient if the skin barrier is overcome. The main source of resistance to penetration and permeation through the skin is the stratum corneum layer of the skin, which is also known as the "horny layer."

The stratum corneum consists of layers of highly flattened keratin-filled cells and is of thin layers of dense, approximately 10-15 microns thick over most of the body. Thus the permeation rate of many drugs through the skin is extremely low. Thus, there is continued interest in the development of strategies to alter the skin barrier to percutaneous absorption of compounds.

Reduction of the skin barrier function is predicted to increase the therapeutic efficacy of dermatological formulation and transdermal devices, by obtaining significant improvements in the kinetics and/or extent of percutaneous absorption. In order to increase the rate at which a drug penetrates through the skin, different strategies have been followed, involving the use of either a physical penetration enhancer (iontophoresis, sonophoresis, heating) or a chemical penetration enhancer, administered along with the drug or in some cases before the drug is applied on the skin ("pretreatment").

Generally, suitable permeation enhancers which promote the percutaneous absorption of a number of drugs is known. These permeation enhancers have been classified according to their mechanism of action. See, Sinha V R, Kaur M P, "Permeation Enhancers for Transdermal Drug Delivery," Drug Dev Ind Pharm. Nov. 2000;26(11):1131-40.

Although permeation enhancers have become widely used in transdermal or topical delivery of drugs, one problem is that no specific permeation enhancer may be considered as suitable for all drugs, as demonstrated above. Moreover, the selection of the most efficient permeation enhancer for a particular drug relies on empirical techniques, the applicability of which is far from universal, and the results are too unpredictable. For example, the selection of an appropriate permeation enhancer will depend on many parameters including:

(1) The specific drug to be administered. A permeation enhancer identified for one specific drug may not be efficient with another drug;

(2) The permeation enhancer concentration. The enhancement effect may be optimal at a given concentration of the permeation enhancer, and may be lowered or even negative under or above this concentration;

(3) The vehicle or carrier. A permeation enhancer may be efficient in a aqueous vehicle for instance, while not efficient in an organic vehicle; and (4) The components of the system. The permeation enhancer may interact with the drug itself, and thus considerably alter the characteristics and the stability of the drug, or with polymers, antioxidants, and the like.

Some approaches to the selection of enhancers formulated into topical systems have been published by Pfister, Yum and Ghosh, "Transdermal and Topical Drug Delivery Systems," Chapter 11: "Chemical means of transdermal drug permeation enhancement," (Interpharm Press, Inc. 1997). However, as demonstrated in a considerable amount of studies, the main principle governing the selection of a permeation enhancer is "trial and error." Accordingly, an optimized transdermal formulation can only be achieved after conducting numerous experiments.

Various permeation enhancers have been reported for transdermal or topical delivery of oxybutynin. For example, U.S. Pat. No. 5,411,740, U.S. Pat. No. 5,500,222, U.S. Pat. No. 5,614,211, each disclose monoglyceride or a mixture of monoglycerides of fatty acids as the preferred permeation enhancer for an oxybutynin transdermal therapeutic system. U.S. Pat. No. 5,736,577 describes a pharmaceutical unit dosage form for transdermal administration of (S)-oxybutynin comprising a permeation enhancer. U.S. Pat. No. 5,834,010 and U.S. Pat. No. 6,555,129 both disclose triacetin as a permeation enhancer for oxybutynin. U.S. Pat. No. 5,747,065 discloses monoglycerides and lactate esters as a permeation enhancing mixture for oxybutynin.

Moreover, U.S. Pat. No. 5,843,468 describe a dual permeation enhancer mixture of lauryl acetate and a glycerol monolaurate for transdermal administration of oxybutynin. U.S. Pat. No. 6,004,578 disclose permeation enhancers selected from the group consisting of alkyl or aryl carboxylic acid esters of polyethyleneglycol monoalkyl ether, and polyethyleneglycol alkyl carboxymethyl ethers for a transdermal matrix drug delivery device comprising oxybutynin. Meanwhile, U.S. Pat. No. 6,267,984 discloses skin permeation enhancer compositions comprising a monoglyceride and ethyl palmitate for transdermal delivery of oxybutynin. U.S. Pat. No. 6,562,368 discloses the use of hydroxide-releasing agent to increase the permeability of skin or mucosal tissue to transdermally administered oxybutynin. As mentioned above, currently, the approach to finding a suitable permeation enhancer for a particular drug is through trial and error.

Urea is a natural substance and a final metabolite of proteins in the body. The value of urea in pharmaceutical and cosmetic preparations has been recognized since the early days of folk medicine, e.g., urea aids in debridement, dissolves the coagulum and promotes epithelialization when used in a concentration of approximately 10-15 percent; at higher concentrations, e.g. above 40 percent, urea is proteolytic and therefore, is commonly used for the treatment of nail destruction and dissolution, urea is also used as an osmotic diuretic.

One remarkable property of urea is the increased water-holding capacity of the stratum corneum in the presence of urea. Urea is mildly keratolytic and increases water uptake in the stratum corneum. This gives the stratum corneum a high water-binding capacity. Accordingly, urea is often used as a skin moisturizer.

Urea is also generally known as a permeation enhancer for certain drugs. However, the percutaneous absorption enhancement by urea is strongly dependent on the cosolvents used. For example, Kim et al. observed that the penetration of ketoprofen was enhanced in the presence of urea in aqueous solutions, whereas in propylene glycol or propylene glycol-ethanol mixtures no enhancement was reported. Moreover, Kim found that the addition of high amounts of urea increases the diffusivity of ketoprofen.

A similar synergetic effect was also demonstrated by Lu et al, who demonstrated that the absorption of leuprolide from human cadaver skin, hairless mouse skin, and shed snake skin was enhanced in the presence of urea and terpenes. These enhancers alone, i.e., without solvent, however, did not significantly enhance permeation. Lu M Y, Lee D. Rao G S, *Percutaneous absorption enhancement of leuprolide,* Pharm. Res. Dec. 1992;9 (12): 1575-9. Similar to the above cited study, the incorporation of urea significantly increases diffusivity of the drug. This kind of solvent dependency was also cited by Williams in "Percutaneous Penetration Enhancers", chapter 10.1: "Urea and its derivatives as penetration enhancers" eds. Smith et al., CRC Press, 1995.

Further, U.S. Pat. No. 5,696,164 and U.S. Pat. No. 6,042,845 both disclose a composition for anti fungal treatment of nails comprising urea in combination with a sulfhydryl containing amino acid or a derivative thereof as permeation enhancer. U.S. Pat. No. 4,996,193 discloses formulations for the topical application of cyclosporin to skin tissue in which urea is used as a permeation enhancer. U.S. Pat. No. 5,015,470 discloses cosmetic and pharmaceutical compositions for inducing, maintaining or increasing hair growth, which contain urea as permeation enhancer. U.S. Pat. No. 5,654,337 discloses a topical formulation for local delivery of anti-inflammatory or antineoplastic agents, in which urea is used to promote gel formation. U.S. Pat. Nos. 5,874,463 and in 6,300,369 both disclose a hydroxy-kojic acid skin peeling composition containing urea as skin-penetrating agent. U.S. Pat. No. 5,879,690 discloses compositions for the topical administration of catecholamines and related compounds to subcutaneous muscle tissue using percutaneous penetration enhancers including urea. U.S. Pat. No. 6,132,760 discloses a transdermal delivery device for testosterone containing urea as a monomer component of the copolymeric pressure sensitive skin adhesive. U.S. Pat. No. 6,162,419 discloses dermatological stabilized ascorbyl compositions containing permeation enhancers of urea or oleic acid.

Similarly, U.S. Pat. No. 6,214,374 discloses use of urea or urea derivatives as permeation enhancers for hormones. U.S. Pat. No. 4,699,777 discloses the synergistic action of combination of urea and 1-dodecyl-azacycloheptan-2-one on albuterol transdermal flux. U.S. Pat. No. 4,895,727 discloses a composition containing urea and a water-soluble zinc-containing compound inducing a reservoir effect in skin and mucous membranes so as to enhance penetration and retention and reduce transdermal flux of topically applied therapeutic and cosmetic pharmacologically active agents. U.S. Pat. No. 5,446,025 discloses a combination of urea, menthol, methyl salicylate and camphor as a cutaneous membrane penetration enhancing mixture for the percutaneous administration of leuprolide.

Urea is also uses as a soluble humectant, i.e., a water binding substance that is capable of retaining large amounts of water (relative to their weight) in the skin, thereby helping to keep the skin smooth and supple. Urea, along with certain amino acids, epidermal lipids and proteins, is known as a constituent of the natural moisturizing factor NMF, produced during the keratinisation process. See, Brian W. Barry "Dermatological Formulations: Percutaneous Absorption", chapter 4, page 147, Marcel Dekker, ISBN: 0-8247-1729-5. Urea gets into the horny layer as an end product of the decomposition of the amino acid, arginine, which is a building block in proteins, during the keratinisation process. Urea represents 7% of the NMF in the horny layer. Urea penetrates and re-hydrates the stratum corneum.

The addition of urea to dermatological preparations is known to increase the penetration of corticosteroids, which are attributed to urea's ability to increase skin hydration after application. It also has anti-pruritic activity (stops itching) based on local anaesthetic effects.

The proteolytic characteristics of urea are also well recognized, where depending on the concentration, urea modifies the structure of amino-chains as well as of polypeptides. This is significant for skin moisturizing since a correlation exists between water content and amino acid content in skin—the drier the skin the lower the share of dissolved amino acids. Urea also helps in higher concentrations (10%) to reduce scales and calluses.

Numerous studies in which urea exhibited permeation enhancement effect is disclosed in Ghosh, Pfister and Yum in "Transdermal and Topical Drug Delivery Systems", Chapter 11: "Chemical means of transdermal drug permeation enhancement" (Interpharm Press, Inc. 1997). The particular agents for which urea has been demonstrated to be a suitable permeation enhancer are shown below.

| Compound | Vehicle | Enhancer and weight percent | Membrane type[a] | RE[b] | References |
| --- | --- | --- | --- | --- | --- |
| Indomethacin | Patches | (A) Urea: 15%<br>(B) Urea/octanol (1:1): 10%<br>(C) Urea/PG (3:1): 20% | Human | (A) 2.5<br>(B) 3.25<br>(C) 3.75 | Kanikkhannan et al. (1994) |
|  | Petrolatum ointment | Various cyclic ureas 5% | (A) Shed snake<br>(B) Hairless mouse | (A) up to 2.0 | Wong et al. (1989) |
| Ketoprofen | Aqueous | Urea 20% | Rat | 1.5 | Kim et al. (1993) |
|  | PG | Urea 10% |  | 3.1 |  |
|  | Ethanol/PG/H2O | Urea 36% |  | 3.5[c] |  |
| Leuprolide | Hydrogel | Urea 10% | Human<br>Shed snake | 10 | Lu et al. (1992) |
| Insulin | Aqueous with surfactants | Urea 10% | Human | 2.11-3.80 | Rao and Misra (1994) |

-continued

| Compound | Vehicle | Enhancer and weight percent | Membrane type[a] | RE[b] | References |
|---|---|---|---|---|---|
| 5-fluorouracil | Propylene glycol | (A) 1-dodecyl urea<br>(B) 1,3-didodecyl urea<br>(C) 1,3-diphenyl urea | Human | (C) up to 9.0 | Williams and Barry (1989) |

[a]In vitro unless otherwise stated;
[b]Relative Enhancement factor (RE) compared to control;
[c]Diffusivities are compared;
[d]No data given
Note:
PG = Propylene glycol Interestingly, Ghosh, Pfister & Yum conducted a similar work on other chemical classes of penetration enhancers, i.e., hydrocarbons, alkanols and alkenols, acids, esters, alkyl amino esters, amides, sulfoxides, cyclodextrins, terpenes, pyrrolidones, Azone® and analogues, phospholipids, and surfactants. Examination of these comparative tables reveals that one particular active compound may present enhanced transdermal permeation when in contact with various permeation enhancers. For example, indomethacin for instance may be enhanced by urea, but also by nonane, 1-nonanol, oleic aciddecyl-(N,N-dimethylamino)isopropionate, tetrahydrothiophene-1-oxide and analogues, d-limonene, pyrrolidone analogues, Azone® and analogues.

As can be seen from the chart below, although different enhancers may be effective for enhancing penetration of particular drugs, the enhancement factor and efficacy can vary greatly.

| | Enhancement factor[a] | | | |
|---|---|---|---|---|
| Drugs | Propyl myristate | Propyl oleate | Azone | Decylmethyl sulfoxide |
| Progesterone | 4.56 | 5.36 | 5.96 | 11.04 |
| Estradiol | 9.33 | 14.62 | 20.17 | 12.59 |
| Hydrocortisone | 4.57 | 5.01 | 61.3 | 25.23 |
| Indomethacin | 3.77 | 4.67 | 14.49 | 15.67 |

[a]Enhancement factor = (Normalized skin permeation rate) with enhancer/ (Normalized skin permeation rate) without enhancer.

See, Chien, "Developmental Concepts and Practice in Transdermal Therapeutic Systems" in Transdermal Controlled Systemic Medications, Marcel Dekker Inc., New York, 1987, pages 25-81, which is incorporated herein by reference.

In view of these results, it is known that a penetration enhancer increases the permeation of different compounds to different degree. For example, a particular permeation enhancer might be very adequate for a particular drug, but might not increase the permeability of a different drug. This is explained by the fact that transdermal permeability is mainly influenced by both the interaction of the permeants with the enhancers and by physicochemical properties of the permeants. Illustrative of these findings, Chien published the dependence of the enhancement factor for the skin permeation of progesterone on the alkyl chain length of saturated fatty acid in "Transdermal Controlled Systemic Medications." He found major enhancement effect using caproic acid (C8), however the same author discloses in U.S. Pat. No. 5,145,682 that the better enhancer for estradiol is decanoic acid (C10). Thus, the efficacy of a skin penetration enhancer for a specific active agent is a function of the type, concentration, and how the penetration enhancer is released from the devices.

One problem in the art is that the concept of a "universal" enhancer for a transdermal penetration enhancement effect for any active agent or drug is nonexistent. Thus, selection of a permeation enhancer is ordinarily drug specific and determined by trial and error through experimentation. No general guidelines exist for ensuring success in selecting an appropriate enhancer for a specific drug to be delivered from a transdermal device (Hsieh 1994).

Further, the science of optimizing topical formulations is not predictive from one drug to another and permeation enhancers can produce a wide range of enhancement factors across drugs having different physicochemical properties. Rather, this is a process that requires extensive experimental work: adequate permeation rate across the skin can be achieved only by testing different types of compounds at different concentrations.

As a testament to this "trial and error" approach, below is a chart that illustrates various potential permeation enhancers that have been tested to promote the transdermal absorption of oxybutynin.

| Oxybutynin concentration [% w/w] | Enhancer concentration [% w/w] | Absorbed daily amount [µg/cm²/24 h] | Enhancement Ratio ER | Steady-state flux [µg/cm²/h] | Enhancement Ratio ER |
|---|---|---|---|---|---|
| 3.0 | LA 1 | 39.15 | 0.86 | 1.78 | 0.76 |
| 3.0 | OAL 1 | 37.83 | 0.83 | 1.99 | 0.85 |
| 5.0 | EO 5 | 24.90 | 0.86 | 1.35 | 0.81 |
| 5.0 | DBP 5 | 24.32 | 0.84 | 1.18 | 0.71 |
| 5.0 | GML 5 | 35.00 | 0.95 | 1.70 | 0.84 |
| 5.0 | PGML 5 | 23.54 | 0.64 | 1.33 | 0.66 |
| 3.0 | EO 1 | 33.78 | 1.19 | 1.66 | 1.12 |
| 3.0 | EO 3 | 28.75 | 1.01 | 1.52 | 1.03 |

-continued

| Oxybutynin concentration [% w/w] | Enhancer concentration [% w/w] | Absorbed daily amount [μg/cm$^2$/24 h] | Enhancement Ratio ER | Steady-state flux [μg/cm$^2$/h] | Enhancement Ratio ER |
|---|---|---|---|---|---|
| 3.0 | AG 1 | 15.25 | 0.50 | 0.93 | 0.57 |
| 3.0 | AG 3 | 18.67 | 0.61 | n.a. | n.a. |
| 3.0 | NMP 5 | 37.51 | 0.81 | 2.34 | 0.95 |
| 3.0 | NMP 10 | 30.12 | 0.65 | n.a. | n.a. |

LA: lauryl alcohol;
OA: oleyl alcohol;
EO: ethyl oleate;
DBP: dibutyl phtalate;
GML: glycerol monolaurate;
PGML: propylene glycol monolaurate;
AG: acetyl glycerol;
NMP: N-methyl pyrrolidone.

As can be seen, the absorption rate, enhancement ratio, and steady state flux for these penetration enhancers vary greatly. Thus, there is a need for an improved topical or transdermal composition that adequately delivers anticholinergic agents, such as oxybutynin, and which enhances permeation of the anticholingeric agents across the dermal or mucosal barrier.

SUMMARY OF INVENTION

The purpose and advantages of the present invention will be set forth in and be apparent from the description that follows, as well as will be learned by practice of the invention. Additional advantages of the invention will be realized and attained by the practice of the compositions and methods particularly pointed out in the written description and claims hereof, as well as from the appended figures.

To achieve these and other advantages, and in accordance with the invention is a composition for the topical or transdermal administration of a therapeutically effective anticholinergic or antispasmodic agent. Particularly, the invention provides a composition for enhancing the permeation or penetration of anticholinergic or antispasmodic agents across the dermal or mucosal surfaces of a mammalian subject. It has been surprisingly found that a composition comprising a urea-containing compound increases the penetration of the anticholinergic agent across the dermal or mucosal surfaces of a subject. It has also been found that the composition of the invention provides a steady plasma concentration of drug and avoids peak concentrations. Advantageously, the avoidance of peak concentrations is associated with reduced occurrences of unwanted and undesirable side effects.

In one aspect of the invention a composition for topical or transdermal administration is provided which comprises a therapeutically effective amount of an anticholinergic or antispasmodic agent or a functional derivative thereof, a urea-containing compound in an amount sufficient for enhancing permeation of the anticholinergic agent, and a carrier system suitable for topical or transdermal drug delivery. The phrase "therapeutically effective" refers to a non toxic but sufficient amount of a compound to provide the desired therapeutic effect.

The urea containing compound has the general formula

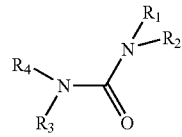

wherein $R_1$, $R_2$, $R_3$, and $R_4$ is a functional group selected from the group including hydrogen, an alkyl group, a thiol group, an aromatic group, a carboxyl group, a carbonyl group, an ether linkage, an ester group, an amine group, an allophanamide, a glycolyl group, a carbonic acid, or any combination thereof.

For the purpose of illustration and not limitation the urea-containing compound can be urea, or a derivative or analogue thereof including 1,3-Dimethylurea, 1,1-Diethylurea, 1-Acetyl-1-phenylurea, Isopropylideneurea, Allophanic acid, Hydantoic acid, Allophanoyl, Pyrrolidone carboxylic acid, Biuret, Thiobiuret, Dithiobiuret, Triuret and 2-(3-Methylureido)-1-naphthoic acid.

The anticholinergic agent can be oxybutynin or a pharmaceutically acceptable salt thereof. For example, oxybutynin salts include acetate, bitartrate, citrate, edetate, edisylate, estolate, esylate, fumarate, gluceptate, gluconate, glutamate, hydrobromide, hydrochloride, lactate, malate, maleate, mandelate, mesylate, methylnitrate, mucate, napsylate, nitrate, pamoate, pantothenate, phosphate, salicylate, stearate, succinate, sulfate, tannate and tartrate.

Alternatively, other anticholinergic or antispasmodic agents may be used such as tolterodine, fesoterodine, duloxetine, solifenacin, trospium, botox, flavoxate, propantheline, dicyclomine, phenylpropanolamine.

Alternatively, other agents may be used such as nitric oxide derivatives of flurbiprofen (a prostaglandin synthesis inhibitor) and imipramine (an antidepressant with marked systemic antimuscarinic actions).

The carrier of the invention is suitable for transdermal or topical administration or delivery of the anticholinergic or antispasmodic agent. The carrier comprises at least one of an alcohol, a polyalcohol, a monoalkyl ether of diethylene glycol, a tetraglycol furol, or water. Preferably, the carrier comprises the combination of an alcohol, a polyalcohol, a monoalkyl ether of diethylene glycol or a tetraglycol furol, and water, or the combination of a polyalcohol, a monoalkyl ether of diethylene glycol or a tetraglycol furol, and water.

The monoalkyl ether of diethylene glycol can be diethylene glycol monomethyl ether, diethylene glycol monoethyl ether or a mixture thereof. The polyalcohol can be propylene glycol, dipropylene glycol or a mixture thereof, and the alcohol can be ethanol, propanol, isopropanol, 1-butanol, 2-butanol or a mixture thereof. The tetraglycol furol can be glycofurol.

The composition is in a form suitable for transdermal or transmucosal administration. Preferably, the formulation is in the form of a gel. Alternatively, however, the formulation may be in the form of a spray, ointment, lotion, emulsion, aerosol, patch, foam, microsphere, nanosphere, microcapsule, nanocapsule, liposome, micelle, or cream. The composition may be administered via buccal and sublingual tablets, suppositories, vaginal dosage forms, or other passive or active transdermal devices for absorption through the skin or mucosal surface.

In another aspect of the invention, a method is provided for treating urinary incontinence in a subject. The invention provides for the administration of a therapeutic composition comprising an anticholinergic or antispasmodic drug, a permeation enhancer comprising urea or a derivative or analogue thereof, and a hydroalcoholic carrier. The phrase "permeation enhancer" as used herein means an agent which improves the rate of percutaneous transport of active agents across the skin or use and delivery of active agents to organisms such as animals, whether for local application or systemic delivery.

The anticholinergic agent or antispasmodic agent can be for example, oxybutynin or a salt thereof. The oxybutynin can be in the form of a racemate, an S-enantiomer, or an R-enantionmer. Generally, the daily dosage of racemic oxybutynin is about 1 to 20 milligrams over a 24-hour period, and the daily dosage of an individual enantiomer of oxybutynin is preferably lower than the corresponding racemate dose. More preferably, the daily dosage for an enantiomer of oxybutynin is about 0.5 to about 15 milligrams over a 24-hour period.

Other agents that are useful for the invention include anticholinergic or antispasmodic agents such as tolterodine, fesoterodine, duloxetine, solifenacin, trospium, botox, flavoxate, propantheline, dicyclomine, or phenylpropanolamine, imipramine, niric oxide derivatives of flurbiprofen.

In accordance with the invention, the method provides symptomatic treatment of bladder instability and urinary incontinence including hyperactivity of the detrusor muscles, frequent urge to urinate, decreased bladder capacity, increased urination during the night, urgent urination, involuntary urination with or without the urge to urinate, and/or painful or difficult urination.

Advantageously, the compositions and methods of the invention provide a steady plasma concentration of anticholinergic or antispasmodic agent, avoids undesirable peaks in drug concentration, and/or reduces the incidences of unwanted, undesirable side effects such as dry mouth, accommodation disturbances, nausea and dizziness.

DETAILED DESCRIPTION OF THE PREFERRED EMBODIMENTS

Figure 1:
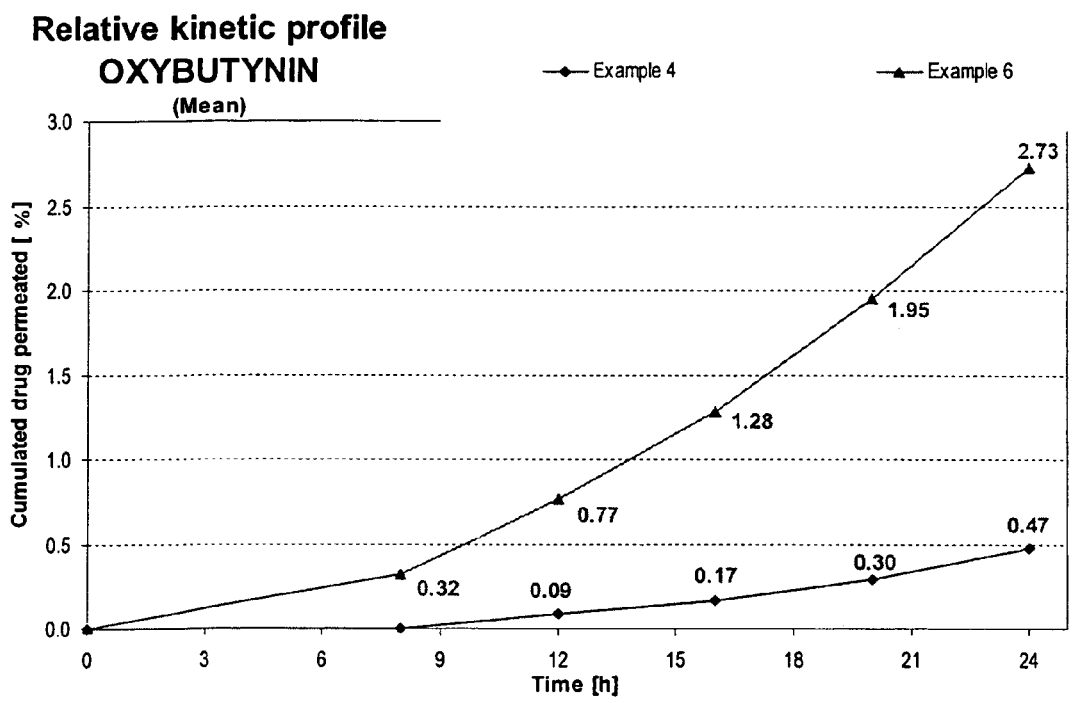
FIG. 1 is a graph illustrating the results from an in-vitro 24-hour comparative permeation study comparing permeation of a composition comprising oxybutynin, urea, and a carrier, and a composition comprising oxybutynin, a carrier, and no urea.

In one aspect of the invention, a novel topical or transdermal composition comprising a therapeutically effective anticholinergic or antispasmodic agent is provided. Particularly, the invention provides a composition for enhancing the permeation or penetration of anticholinergic or antispasmodic agents across the dermal or mucosal surfaces of a mammalian subject. The term "transdermal" as used herein intends to include both transdermal (or "percutaneous") and transmucosal administration, i.e., delivery by passage of a drug through the skin or mucosal tissue and into the bloodstream.

It has been surprisingly found that a composition comprising a urea-containing compound increases the penetration of the anticholinergic agent or antispasmodic agent across the dermal or mucosal surfaces of a subject.

It has also been found that the composition of the invention provides a steady plasma concentration of drug and avoids peak concentrations of the drug. Advantageously, the avoid ance of peak concentrations is associated with reduced occurrences of unwanted and undesirable side effects.

In one aspect of the invention a composition for topical or transdermal administration is provided which comprises a therapeutically effective amount of an anticholinergic agent or antispasmodic agents or functional derivatives thereof, a urea-containing compound in an amount sufficient for enhancing permeation of the anticholinergic agent, and a carrier system suitable for topical or transdermal drug delivery.

The urea containing compound has the general formula

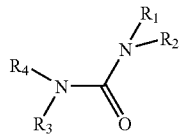

wherein $R_1$, $R_2$, $R_3$, and $R_4$ is a functional group selected from the group including hydrogen, an alkyl group, a thiol group, an aromatic group, a carboxyl group, a carbonyl group, an ether linkage, an ester group, an amine group, an allophanamide, a glycolyl group, a carbonic acid, or any combination thereof.

For the purpose of illustration and not limitation the urea-containing compound can be urea, a derivative, or an analogue, thereof including 1,3-Dimethylurea, 1,1-Diethylurea, 1-Acetyl-1-phenylurea, Isopropylideneurea, Allophanic acid, Hydantoic acid, Allophanoyl, Pyrrolidone carboxylic acid, Biuret, Thiobiuret, Dithiobiuret, Triuret and 2-(3-Methylureido)-1-naphthoic acid or a derivative thereof as illustrated in Table 1 below.

TABLE 1

Urea Derivatives and Analogues

[Structures shown: 1,3-Dimethylurea; Allophanic Acid; Biuret; 1,1 Diethylurea; Hydantoic acid; Thiobiuret; 1-Acetyl-1-phenylurea; Allophanoyl; Dithiobiuret; Isopropylideneurea; Pyrrolidone carboxylic acid; Triuret; Lauryl urea; 4-Thiotriuret]

Preferably, the urea-containing compound is present in the composition in an amount of between about 1% to about 20% of the composition.

The anticholinergic or antispasmodic agent can be oxybutynin or a pharmaceutically acceptable salt thereof. Examples of some oxybutynin salts are acetate, bitartrate, citrate, edetate, edisylate, estolate, esylate, fumarate, gluceptate, gluconate, glutamate, hydrobromide, hydrochloride, lactate, malate, maleate, mandelate, mesylate, methylnitrate, mucate, napsylate, nitrate, pamoate, pantothenate, phosphate, salicylate, stearate, succinate, sulfate, tannate and tartrate. The oxybutynin may be as a racemate or a single isomer such as the S-enantionmer or R-enantiomer.

Alternatively, other anticholinergic or antispasmodic agents may be used such as tolterodine, fesoterodine, duloxetine, solifenacin, trospium, botox, flavoxate, propantheline, dicyclomine, phenylpropanolamine; other agents such as nitric oxide derivatives of flurbiprofen (a prostaglandin synthesis inhibitor) and imipramine (an antidepressant with marked systemic antimuscarinic actions) may be used, as shown in Table 2 infra. Preferably, the anticholinergic or antispasmodic agent is oxybutynin.

Advantageously, these agents as well as oxybutynin have been indicated for conditions including overactive bladder and urinary incontinence to mention a couple. Thus, the composition of the invention, which comprises a urea-containing compound, which has been found to increase the permeation of these drugs, is not only novel but is desirable since compositions can now be formulated containing lower amounts of drug.

A transdermal or topical composition comprising anticholinergic or antispasmodic agents, such as oxybutynin or the aforementioned agents, is very desirable. As transdermal and topical compositions bypass the gastrointestinal tract, and are not subject to the "first pass hepatic effect," the blood concentration peaks of the anticholinergic or antispasmodic agent avoided. It has been found that the blood concentration peaks of substances such as oxybutynin often lead to the occurrence of undesirable side-effects, such as dry mouth, accommodation disturbances, nausea and dizziness. Accordingly, the one advantage of bypassing the first-pass metabolism in the liver is the increased bioavailability of drug in comparison to oral administration of drug. As the bioavailability is increased for transdermal or topical administered drugs, the total daily dosages that are necessary for reaching a desired therapeutic effect is reduced. Moreover, in conjunction with the enhanced permeation of the present compositions comprising anticholinergic or antispasmodic agents and a urea-containing compounds, the greater permeability, and thus bioavailability of the drug in comparison, the advantages for the transdermal or topical composition of the present invention are even greater.

Generally, the composition comprises the anticholinergic or antispasmodic agent in an amount sufficient to provide a suitable daily dose to a subject in need. Accordingly, the amount of anticholinergic or antispasmodic agent in the composition may vary and will depend on a variety of factors, including the disease or condition to be treated, the nature and activity of the particular active agent, the desired effect, possible adverse reactions, the ability and speed of the active agent to reach its intended target, as well as other factors within the particular knowledge of the patient and physician. The preferred compositions, however, will comprise the anticholinergic or antispasmodic agent in an amount of about 0.1% w/w to 20% w/w, more preferably about 0.5% w/w to 10%, and most preferably about 1% w/w to 5% w/w.

In one preferred embodiment of the invention, the daily dosage of racemic oxybutynin is between about 1 to 20 milligrams over a 24-hour period. In another preferred embodiment, the daily dosages of an individual enantiomer of oxybutynin is between about 0.5 to about 15 milligrams over a 24-hour period.

In accordance with the invention, the carrier is suitable for transdermal or topical administration or delivery of the anticholinergic or antispasmodic agent. The carrier comprises at least one of an alcohol, a polyalcohol, a monoalkyl ether of diethylene glycol, a tetraglycol furol, or water. The phrase "monoalkylether of diethylene glycol" refers to a substance having a general formula $C_4H_{10}O_3(C_nH_{2n+1})$, wherein n is 1-4. The term "tetraglycol" refers to glycofurol, or tetrahydrofurfuryl alcohol. Further, the term "glycol" encompasses a broad range of chemicals including but not limited to propylene glycol, dipropylene glycol, butylene glycol, and polyethylene glycols having general formula $HOCH_2(CH_2OH)_n CH2OH$ wherein the number of oxyethylene groups represented by n is between 4 to 200.

Preferably, the monoalkyl ether of diethylene glycol is diethylene glycol monomethyl ether, diethylene glycol monoethyl ether or a mixture thereof, and more preferably is diethylene glycol monoethyl ether. Preferably, the polyalcohol is propylene glycol, dipropylene glycol or a mixture thereof, and more preferably is propylene glycol. Preferably, the alcohol is ethanol, propanol, isopropanol, 1-butanol, 2-butanol or a mixture thereof, and more preferably is ethanol. Preferably, the monoalkyl ether of diethylene glycol is present in an amount betweeen about 1 to 15% of the formulation, the polyalcohol is present in an amount between about 1 to 15% of the formulation, and the alcohol is present in an amount of between about 5 to 80% of the formulation. Water can be added to constitute the balance of the carrier.

Other useful carriers include the combination of a polyalcohol and either a monoalkyl ether of diethylene glycol or a tetraglycol furol. A preferred polyalcohol is propylene glycol. In this carrier, the relative amounts of polyalcohol to monoalkyl ether of diethylene glycol or tetraglycol furol is about 1:1 to 10:1 and preferably 2.5:1 to 7:1. The amount of polyalcohol can be from 1 to 50% by weight of the carrier, with the monoalkyl ether of diethylene glycol or tetraglycol furol being present in an amount of 1 to 50% and preferably from 2.5 to 25%. Other solvents from the types disclosed herein can be added to these carriers if desired, but it is not necessary to have more than three or four components in the carrier in addition to the water that constitutes the balance. The permeation ability of these carriers can be enhanced by the presence of urea or the urea derivatives disclosed herein.

The composition is in a form suitable for transdermal or transmucosal administration. Preferably, the formulation is a gel. Alternatively, however, the formulation may be in the form of a spray, ointment, aerosol, lotion, solution, emulsion, foam, microsphere, nanosphere, microcapsule, nanocapsule, liposome, micelle, cream, patch, as well as other topical or transdermal forms known in the art.

The composition may be applied directly or indirectly to the skin or mucosal surfaces such as by, for example and not limitation, buccal and sublingual tablets, suppositories, vaginal dosage forms, transdermal patch, bandage, or other occlusive or non-occlusive dressing, or other passive or active transdermal devices for absorption through the skin or mucosal surface of a subject. The phrase "non-occlusive" as used herein refers to a system that does not trap nor segregate the skin from the atmosphere by means of for instance a patch device, a fixed reservoir, an application chamber, a tape, a bandage, a sticking plaster, or the like, which remains on the skin at the site of application for a prolonged period of time.

The composition of the invention can be in a variety of forms. For purpose of illustration and not limitation, the various possible forms for the present composition include gels, ointments, creams, lotions, microspheres, liposomes, micelles, and transdermal patches.

Ointments are generally semisolid preparations typically based on petrolatum or other petroleum derivatives. The phrase "semi-solid" formulation means a heterogeneous system in which one solid phase is dispersed in a second liquid phase. They generally provide optimum drug delivery, and, preferably, emolliency. Oleaginous ointment bases include, for example, vegetable oils, fats obtained from animals, and semisolid hydrocarbons obtained from petroleum. Emulsifiable ointment bases contain little or no water and may comprise anhydrous lanolin or hydrophilic petrolatum. Emulsion ointment bases are either water-in-oil (W/O) emulsions or oil-in-water (O/W) emulsions, and may include, for instance, cetyl alcohol, glyceryl monostearate, lanolin and stearic acid.

Preferred water-soluble ointment bases are prepared from polyethylene glycols of varying molecular weight.

Creams are generally viscous liquids or semisolid emulsions, e.g., oil-in-water or water-in-oil. Cream bases are typically water-washable, and comprise an oil phase, an emulsifier and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally comprises a humectant. The emulsifier in a cream formulation is generally a nonionic, anionic, cationic or amphoteric surfactant.

Gels are semisolid, suspension-type systems. Single-phase gels comprise macromolecules (polymers) distributed substantially uniformly throughout the carrier liquid, which is typically aqueous. However, gels preferably comprise alcohol and, optionally, an oil. Preferred polymers, also known as gelling agents, are crosslinked acrylic acid polymers, polyethylene oxides, polyoxyethylene-polyoxypropylene copolymers and polyvinylalcohol; cellulosic polymers (hydroxypropyl cellulose, hydroxyethyl cellulose, hydroxypropyl methylcellulose, hydroxypropyl methylcellulose phthalate, methyl cellulose); gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

Lotions are generally defined as preparations to be applied to the skin surface without friction. They are typically liquid or semi-liquid preparations in which solid particles, including the active agent, are present in a water or alcohol base. Lotions are usually suspensions of solids, and preferably, for the present purpose, comprise a liquid oily emulsion of the oil-in-water type. Lotions are preferred for treating large body areas, due to the ease of applying a more fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose, sodium carboxymethyl-cellulose, and the like.

Liposomes are microscopic vesicles having a lipid wall comprising a lipid bilayer, and can be used as drug delivery systems herein as well. Generally, liposome formulations are preferred for poorly soluble or insoluble pharmaceutical agents. Liposomal preparations for use in the instant invention include cationic (positively charged), anionic (negatively charged) and neutral preparations. Cationic and anionic liposomes are readily available. or can be easily prepared using readily available materials such as materials include phosphatidyl choline, cholesterol, phosphatidyl ethanolamine, dioleoylphosphatidyl choline (DOPC), dioleoylphosphatidyl glycerol (DOPG), diopalmitoylphosphatidyl choline (DPPC), dipalmitoylphosphatidyl glycerol (DPPG), dioleoylphoshatidyl ethanolamine (DOPE), among others. Methods for making liposomes using these materials are well known in the art.

Micelles, as known in the art, comprise surfactant molecules arranged such that their polar headgroups form an outer spherical shell, while their hydrophobic, hydrocarbon chains are oriented towards the center of the sphere, forming a core. Micelles form in an aqueous solution containing surfactant at a high enough concentration so that micelles naturally result. Surfactants useful for forming micelles include, but are not limited to, potassium laurate, sodium octane sulfonate, sodium decane sulfonate, sodium dodecane sulfonate, sodium lauryl sulfate, docusate sodium, decyltrimethylammonium bromide, dodecyltrimethylammonium bromide, tetradecyltrimethylammonium bromide, tetradecyltrimethylammonium chloride, dodecylammonium chloride, polyoxyl 8 dodecyl ether, polyoxyl 12 dodecyl ether, nonoxynol 10 and nonoxynol 30. Micelle formulations can be used in conjunction with the present invention either by incorporation into the reservoir of a topical or transdermal delivery system, or into a formulation to be applied to the body surface.

Microspheres generally encapsulate a drug or drug-containing formulation. They are generally although not necessarily formed from lipids, preferably charged lipids such as phospholipids. Preparation of lipidic microspheres is well known in the art and described in the pertinent texts and literature.

As mentioned above, the composition may be in the form of a transdermal patch. Generally, transdermal patches comprise an adhesive layer or matrix comprising the a composition or formulation, a backing layer that is impermeable to the composition or formulation and adhesive, and a protective liner releasably attached to the adhesive layer such that the composition or formulation is covered by the liner and unexposed until the protective liner is peeled off by the patch user. Typically, the patch adhesive layer or matrix serves as the carrier for the active agent or active agents to be administered to the patch user. Alternatively, additional layers may be included between the patch adhesive or matrix layer and the backing layer to include additional active agents, or non-toxic polymers well known in the art used to carry drugs or act as rate-controlling membranes.

The composition of the invention may also comprise various additives, as known to those skilled in the art. For instance, solvents, humectant, opacifiers, antioxidants, fragrance, colorant, gelling agents, thickening agents, stabilizers, surfactants, antimicrobial agents, and the like, may be added to the composition.

For the purpose of illustration suitable solvents include, but are not limited to, ethanol, isopropanol, glycol, glycofurol, dimethyl isosorbide, diethylene glycol alkyls ethers, polyethylene glycols, and ethoxylated alcohol.

Antimicrobial agents may be added to the present invention to prevent spoilage upon storage, i.e., to inhibit growth of microbes such as yeasts and molds. Suitable antimicrobial agents are typically selected from the group consisting of the methyl and propyl esters of p-hydroxybenzoic acid (i.e., methyl and propyl paraben), sodium benzoate, sorbic acid, imidurea, and combinations thereof.

Gelling agents may include for example carbomer, carboxyethylene or polyacrylic acid such as carbomer 980 or 940 NF, 981 or 941 NF, 1382 or 1342 NF, 5984 or 934 NF, ETD 2020, 2050, 934P NF, 971P NF, 974P NF and carbomer derivatives; cellulose derivatives such as ethylcellulose, hydroxypropylmethylcellulose (HPMC), ethyl-hydroxyethylcellulose (EHEC), carboxymethylcellulose (CMC), hydroxypropylcellulose (HPC), hydroxyethylcellulose (HEC), natural gums such as arabic, xanthan, guar gums, alginates, polyvinylpyrrolidone derivatives; polyoxyethylene polyoxypropylene copolymers, etc; others like chitosan, polyvinyl alcohols, pectins, veegum grades, and the like. Other suitable gelling agents to apply the present invention include, but are not limited to, carbomers. Alternatively, other gelling agents or viscosants known by those skilled in the art may also be used. The gelling agent or thickener is present from about 0.2 to about 30% w/w depending on the type of polymer, as known by one skilled in the art.

Preservatives such as benzalkonium chloride and derivatives, benzoic acid, benzyl alcohol and derivatives, bronopol, parabens, centrimide, chlorhexidine, cresol and derivatives, imidurea, phenol, phenoxyethanol, phenylethyl alcohol, phenylmercuric salts, thimerosal, sorbic acid and derivatives. The preservative is present from about 0.01 to about 10% w/w depending on the type of compound.

Antioxidants such as but not limited to tocopherol and derivatives, ascorbic acid and derivatives, butylated hydroxyanisole, butylated hydroxytoluene, fumaric acid, malic acid, propyl gallate, metabisulfates and derivatives. The antioxidant is present from about 0.001 to about 5.0% w/w depending on the type of compound.

Buffers such as carbonate buffers, citrate buffers, phosphate buffers, acetate buffers, hydrochloric acid, lactic acid, tartric acid, diethylamine, triethylamine, diisopropylamine, aminomethylamine. Although other buffers as known in the art may be included. The buffer may replace up to 100% of the water amount within the formulation.

Humectants such as glycerin, propylene, glycol, sorbitol. The humectant is present from about 1 to 10% w/w depending on the type of compound.

Sequestering agents such as edetic acid. The sequestering agent is present from about 0.001 to about 5% w/w depending on the type of compound.

Moisturizer such as docusate sodium, polyoxyethylene alkyl ethers, polyoxyethylene castor oil derivatives, polyoxyethylene stearates, polyoxyethylene sorbitan fatty acid esters, sodium lauryl sulfate. The moisturizer is present from about 1.0 to about 5% w/w depending on the type of compound.

Surfactants including anionic, nonionic, or cationic surfactants. The surfactant is present from about 0.1 to about 30% w/w depending on the type of compound.

Emollients such as but not limited to cetostearyl alcohol, cetyl esters wax, cholesterol, glycerin, fatty esters of glycerol, isopropyl myristate, isopropyl palmitate, lecithins, light mineral oil, mineral oil, petrolatum, lanolins, and combinations thereof. The emollient is present from about 1.0 to about 30.0% w/w depending on the type of compound.

Additional permeation enhancer(s) may be incorporated in the formulation, although in a preferred embodiment, urea is administered without any other permeation enhancers. Examples of suitable secondary enhancers (or "co-enhancers") include, but are not limited to, compounds cited in "Percutaneous Penetration Enhancers", eds. Smith et al. (CRC Press, 1995), the content of which is incorporated herein by reference.

For example, sulfoxides such as dimethylsulfoxide and decylmethylsulfoxide; surfactants such as sodium laurate, sodium lauryl sulfate, cetyltrimethylammonium bromide, benzalkonium chloride, poloxamer (231, 182, 184), tween (20, 40, 60, 80) and lecithin; the 1-substituted azacycloheptan-2-ones, particularly 1-n-dodecylcyclazacycloheptan-2-one; fatty alcohols such as lauryl alcohol, myristyl alcohol, oleyl alcohol and the like; fatty acids such as lauric acid, oleic acid and valeric acid; fatty acid esters such as isopropyl myristate, isopropyl palmitate, methylpropionate, and ethyl oleate; polyols and esters thereof such as propylene glycol, ethylene glycol, glycerol, butanediol, polyethylene glycol, and polyethylene glycol monolaurate, amides and other nitrogenous compounds such as dimethylacetamide (DMA), dimethylformamide (DMF), 2-pyrrolidone, 1-methyl-2-pyrrolidone, ethanolamine, diethanolamine and triethanolamine, terpenes; alkanones, and organic acids, particularly salicylic acid and salicylates, citric acid and succinic acid.

Alternatively, other permeation enhancer(s) suitable to be used with the present invention may be known by those skilled in the art. The permeation enhancer is present from about 0.1 to about 30.0% w/w depending on the type of compound. Preferably the secondary permeation enhancers are fatty alcohols and fatty acids, and more preferably fatty alcohols. Preferably, the fatty alcohols have the formula the CH3(CH2)n(CH)mCH2OH wherein n ranges from (8-m) to (16-m) and m=0-2.

The compositions of the present invention may be manufactured by conventional techniques of drug formulation, particularly topical and transdermal drug formulation, which are within the skill of the art. Such techniques are disclosed in "Encyclopedia of Pharmaceutical Technology", $2^{nd}$ Ed., edited by J. Swarbrick and J. C. Boylan, Marcel Dekker, Inc., 2002, the content of which is incorporated herein by reference.

As mentioned above, in one preferred embodiment, the invention provides a composition for the transdermal administration of an anticholinergic or antispasmodic agent, preferably oxybutynin. As pointed out above, the compositions are useful in a variety of contexts, as will be readily appreciated by those skilled in the art. For example, the preferred agent, oxybutynin has been indicated for the treatment of hyperactivity of the detrusor muscle (over activity of the bladder muscle) with frequent urge to urinate, increased urination during the night, urgent urination, involuntary urination with or without the urge to urinate (incontinence), painful or difficult urination. Generally, although not necessarily, these disorders are caused by a neurogenic bladder. See, Guittard et al., U.S. Pat. No. 5,674,895, the content of which is incorporated herein by reference. In addition, oxybutynin may treat other conditions and disorders that are responsive to transdermal administration of oxybutynin, such as detrusor hyperreflexia and detrusor instability. The other anticholinergic or antispasmodic agents have also been indicated for symptomatic treatment of overactive bladder and/or urinary incontinence. Accordingly, in another aspect of the invention a method is provided for the treatment of overactive bladder or urinary incontinence in a subject.

In one embodiment, the method comprises administering to a subject in need, a therapeutic composition comprising an anticholinergic or antispasmodic drug, a permeation enhancer comprising a urea-containing compound, and a hydroalcoholic carrier suitable for topical or transdermal delivery.

The anticholinergic agent or antispasmodic agent can be for example, oxybutynin or a salt thereof. The oxybutynin can be in the form of a racemate, an S-enantiomer, or an R-enantionmer. Other anticholinergic or antispasmodic agents that are useful for the invention are illustrated below in Table 2, which includes tolterodine, fesoterodine, duloxetine, solifenacin, trospium, nitric oxide derivatives of flurbiprofen, botox, flavoxate, imipramine, propantheline, dicyclomine, phenylpropanolamine. Preferably, the composition comprises oxybutynin.

TABLE 2
Actives drugs indicated for treatment of Over Active Bladder and Urge Incontinence
Oxybutynin
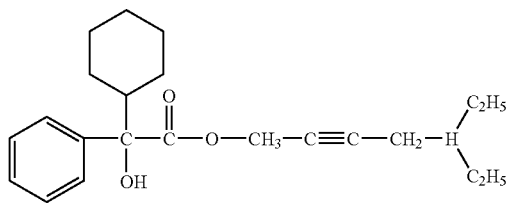
Flavoxate
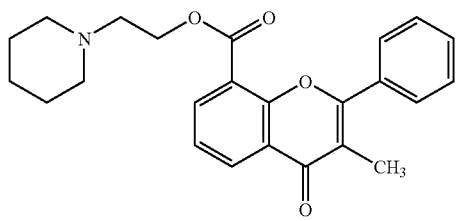
Imipramine
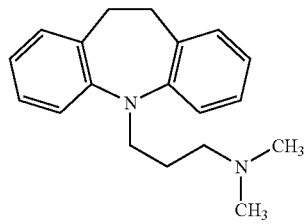
Propantheline
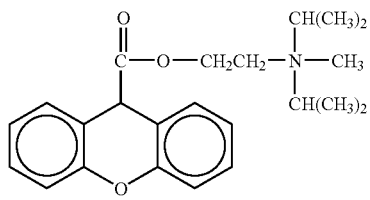
Phenylpropanolamine
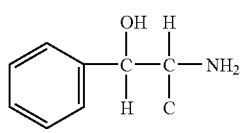
Darifenacin
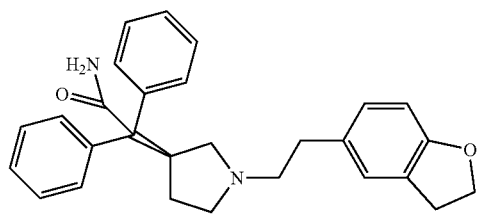
Duloxetine
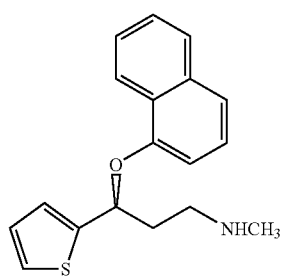

TABLE 2-continued

Actives drugs indicated for treatment of Over Active Bladder and Urge Incontinence Tolterodine tartrate HCT-1026 (NO-flurbiprofen)

Solifenacin succinate    (structure not available)

Preferably, the amount of anticholinergic or antispasmodic agent is between about 0.1 to about 20%, more preferably about 0.5% to about 10%, and most preferably about 1% to about 5% of the composition by weight. Preferably, the agent is oxybutynin or a pharmaceutically acceptable salt thereof. Preferably, the daily dosage of racemic oxybutynin is about 1 to 20 milligrams over a 24-hour period, and preferably, the daily dosage of an individual enantiomer of oxybutynin is preferably lower than the corresponding racemate dose, and about 0.5 to about 15 milligrams over a 24-hour period.

The present method for treating overactive bladder or urge incontinence in a subject provides greater patient compliance. It has been found that the present method not only provides greater bioavailability of the drug associated with the permeation enhancer of urea-containing compound, but also provides a steady plasma drug concentration. Thus, the composition administered to the patient comprises lower amounts of drug to achieve therapeutic effects, i.e., greater bioavailability, and avoids the common peaks in plasma drug concentrations. Additionally, it has been found that the oxybutynin: metabolite ratio is higher than other oxybutynin compositions. Accordingly, the method of the invention advantageously reduces the number of incidences and/or the intensity of common undesirable side-effects associated with oxybutynin administered compositions. Some common undesirable side effects include dry mouth, accommodation disturbances, nausea and dizziness. Thus, the method of the invention will provide greater patient compliance.

Advantageously, the method of the invention provides symptomatic treatment of a number of conditions including hyperactivity of the detrusor muscles, frequent urge to urinate, decreased bladder capacity, increased urination during the night, urgent urination, involuntary urination with or without the urge to urinate (incontinence), an/or painful or difficult urination.

It is to be understood that while the invention has been described in conjunction with the preferred specific embodiments thereof, the foregoing description is intended to illustrate and not to limit the scope of the invention. Other aspects, advantages and modifications will be apparent to those skilled in the art to which the invention pertains.

EXAMPLES

The following examples are merely illustrative of the present invention and they should not be considered as limiting the scope of the invention in any way, as these examples and other equivalents thereof will become apparent to those skilled in the art in light of the present disclosure and the accompanying claims.

Example 1

A gel composed by oxybutynin base 3.00% w/w, ethanol 54.22% w/w, purified water 17.23% w/w, diethylene glycol monoethyl ether 2.50% w/w, propylene glycol 15.0% w/w, hydroxypropylcellulose (KLUCEL™ MF Pharm) 2.00% w/w, butylhydroxytoluene (BHT) 0.05% w/w, hydrochloric acid HCl 0.1M 6.00%, was prepared by dissolving the oxybutynin base in the ethanol/propylene glycoudiethylene glycol monoethyl ether/BHT mixture. Purified water was then added and pH adjusted with hydrochloric acid 0.1N. Hydroxypropylcellulose was then thoroughly dispersed in the hydroalcoholic solution under mechanical stirring at room temperature at a suitable speed ensuring good homogenization of the formulation while avoiding lumps formation and air entrapment until complete swelling.

Example 2

A gel composed by oxybutynin base 3.00% w/w, ethanol 50.72% w/w, purified water 14.73% w/w, diethylene glycol monoethyl ether 2.50% w/w, propylene glycol 15.0% w/w, urea 5.00%, hydroxypropylcellulose (KLUCEL™ MF Pharm) 2.00% w/w, butylhydroxytoluene (BHT) 0.05% w/w, hydrochloric acid HCl 0.1M 7.00%, was prepared according to manufacturing process described in Example 1.

Example 3

A gel composed by oxybutynin base 3.00% w/w, ethanol 34.22% w/w, isopropanol 20.00% w/w, purified water 20.23% w/w, diethylene glycol monoethyl ether 2.50% w/w, propylene glycol 15.0% w/w, hydroxypropylcellulose (KLUCEL™ MF Pharm) 2.00% w/w, butylhydroxytoluene (BHT) 0.05% w/w, hydrochloric acid HCl 0.1M 3.00%, was prepared according to manufacturing process described in Example 1.

Example 4

A gel composed by oxybutynin base 3.00% w/w, ethanol 66.50% w/w, purified water 22.39% w/w, hydroxypropylcellulose (KLUCEL™ MF Pharm) 2.00% w/w, hydrochloric acid HCl 0.1M 6.11%, was prepared according to manufacturing process described in Example 1.

Example 5

A gel composed by oxybutynin base 3.00% w/w, ethanol 30.72% w/w, isopropanol 20.00% w/w, purified water 19.15% w/w, diethylene glycol monoethyl ether 2.50% w/w, propylene glycol 15.0% w/w, urea 5.00% w/w, hydroxypropylcellulose (KLUCEL™ MF Pharm) 2.00% w/w, butylhydroxytoluene (BHT) 0.05% w/w, hydrochloric acid HCl 0.1M 2.58%, was prepared according to manufacturing process described in Example 1.

Example 6

A gel composed by oxybutynin base 3.00% w/w, ethanol 70.00% w/w, purified water 8.19% w/w, urea 5.00% w/w, hydroxypropylcellulose (KLUCEL™ MF Pharm) 2.00% w/w, butylhydroxytoluene (BHT) 0.05% w/w, hydrochloric acid HCl 0.1M 11.76%, was prepared according to manufacturing process described in Example 1.

In Vitro Comparative Studies

In vitro drug permeation and biodistribution experiments through ear pig skin were made using a Franz Vertical Diffusion Cell diffusion chamber. Cutaneous penetration studies in vitro through human skin are limited due to the lack of availability of the human skin. It is largely described in the literature that ear pig skin can be used as the closest model to human skin in the assessment of percutaneous absorption of chemicals.

In Vitro Permeation Experiments

Fresh cadaver ear pig skin obtained from slaughterhouses was processed according to standard operating procedures. The ears were evaluated on their integrity (no bites, scratches or redness) and condition. The skin was excised from the ears with the help of scalpels, avoiding perforations or any damage. The excised skin samples were rinsed with PBS solution and placed on a surface for successive punching of skin disks. The skin disk pieces were mounted between the sections of a vertical diffusion cell having 1.77 sqcm of surface area, the epidermal facing up. 10 or 50 mg of the transdermal devices exemplified previously was applied over the epidermal layer whilst the dermal layer contact with the receptor solution: 2.0% w/v polyoxyethylene 20 oleyl ether (Oleth 20), with PBS, pH 7.4. The receptor chamber was maintained at 35° C. and the studies were conducted under non-occlusive conditions and at 600 rpm of stirring speed. At given time points, samples were withdrawn from the receptor solution and the receptor chamber was immediately refilled with fresh solution. All samples taken from the receptor solution (permeated drug) were analyzed using a high performance liquid chromatography (HPLC) method. The total amount of drug permeated (mcg/sqcm) during the study duration and the transdermal flux (mcg/sqcm/h) were determined for each study.

All the "Drug Permeation Studies" described above, were conducted under the following conditions: Franz Vertical Diffusion Cells (Hanson Research Inc.) were used and ear pig skin was used as experimental model. The receptor solution was 2% w/w polyoxyethylene 20 oleyl ether (Oleth 20), PBS 10 mM, pH 7.4. The experiments were conducted under non-occlusive conditions, at 35° C. and 600 rpm of stirring speed. Prior to the beginning of the study, the skin pieces were mounted on the permeation cells and maintained at 35° C. in contact with the receptor solution. After loading formulation over the skin, at the indicated times, 1 ml of the receptor solution was withdrawn, and the receptor chamber was immediately refilled with fresh solution.

The accompanying figures represent studies which further exemplify the invention described herein. The figures are for the purpose of illustration and not for the limitation of the invention. With reference to FIG. 1, a graph is provided which demonstrates that the composition comprising urea has a 6.7-fold increase in the amount of cumulated, permeated oxybutynin after 24 hours, i.e., 2.73% for Example 6, which comprises 5% urea, versus 0.47% for Example 4 for the reference formulation, not containing urea.

Figure 2:
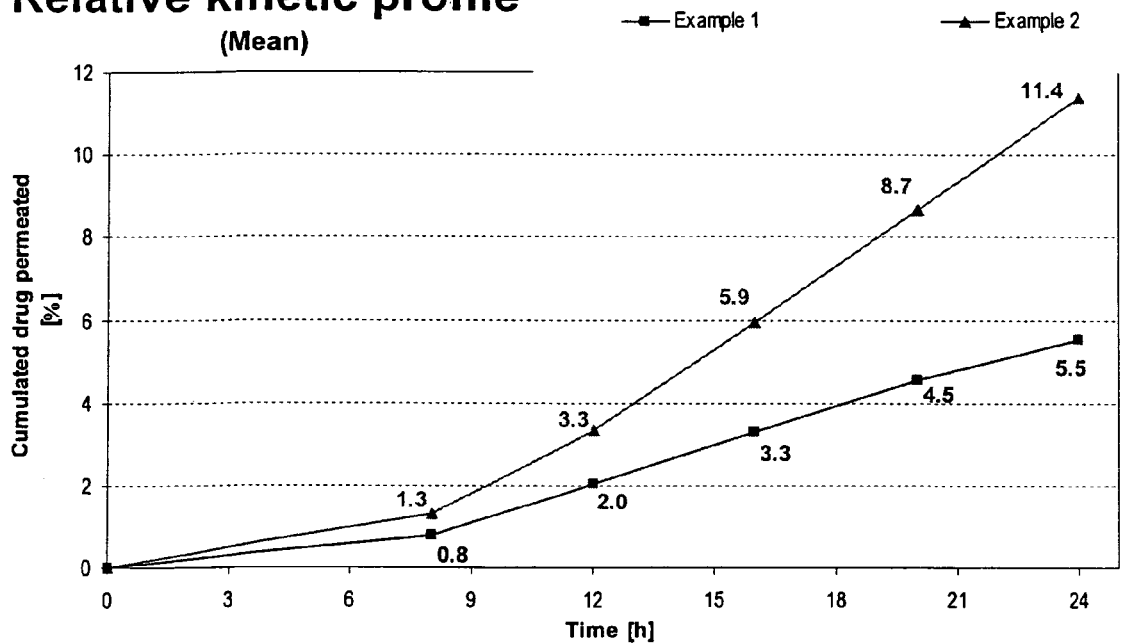
FIG. 2 is a graph illustrating the results of an in-vitro 24-hour comparative permeation study of a composition comprising oxybutynin, a hydroalcoholic carrier, and solvents, and a composition comprising oxybutynin, urea, a hydroalcoholic carrier and solvents.

Referring to FIG. 2, a graph illustrates the results of a 24-hour in vitro comparison permeation study comparing a composition comprising oxybutynin, a hydroalcoholic carrier, additional solvents, i.e., diethylene glycol monoethyl ether and propylene glycol, and no urea, to a composition comprising oxybutynin, a hydroalcoholic carrier, additional solvents, and urea. As shown, after 24 h permeation, the amount of cumulated permeated oxybutynin is significantly higher for Example 2, which comprises urea in an amount of 5% than Example 1, the reference composition which does not contain any urea. The results show a permeation of 11.4% versus 5.5%, respectively.

Figure 3:
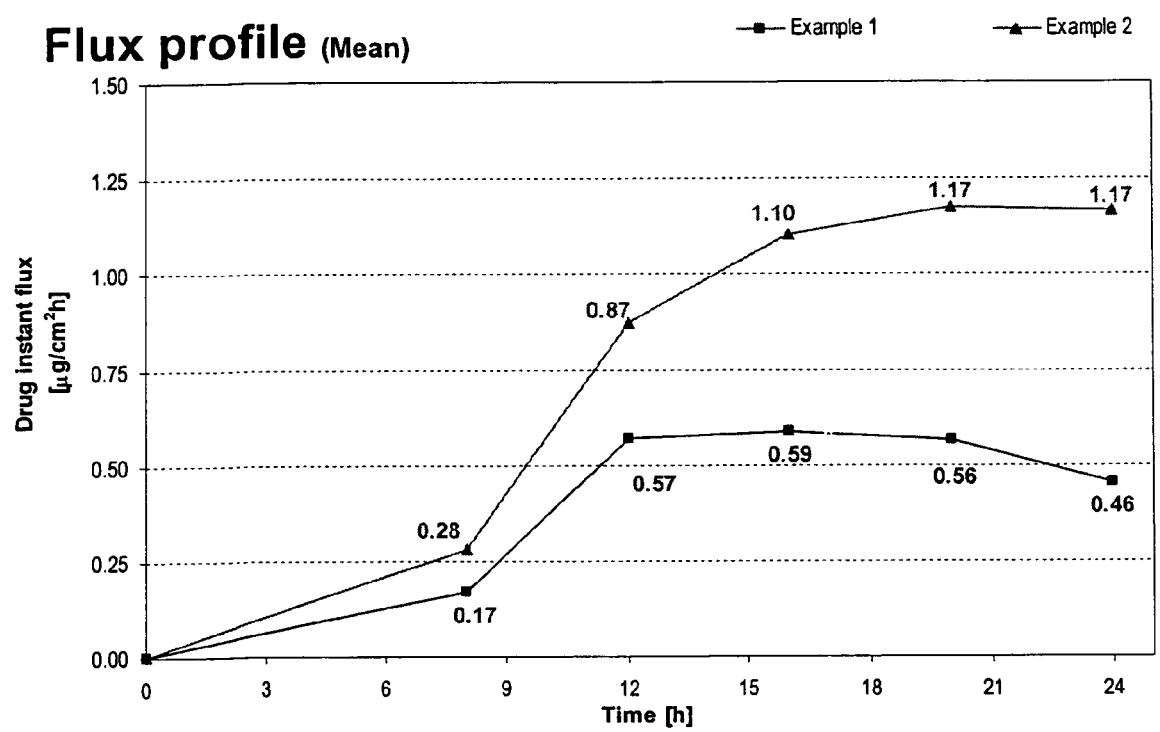
FIG. 3 is a graph illustrating the drug flux profiles of the compositions of FIG. 2.

FIG. 3 illustrates that the maximal transdermal oxybutynin flux is almost 2 times higher in Example 2 than in Example 1, 1.17 µg/cm$^2$h versus 0.59 µg/cm$^2$h, respectively. Additionally, the results show the maximal transdermal oxybutynin flux is reached after 16 hours for Example 1, which contains no urea, and the maximal transdermal oxybuytnin flux is reached after at least 20 hours in Example 2. Accordingly, the presence of urea in the composition, enhances the transdermal oxybutynin permeation, and also delays oxybutynin maximal transdermal instant flux and sustains the oxybutynin maximal transdermal instant flux. This can be responsible for sustained oxybutynin plasmatic levels in vivo after multiple application of a composition of the present invention.

Figure 4:
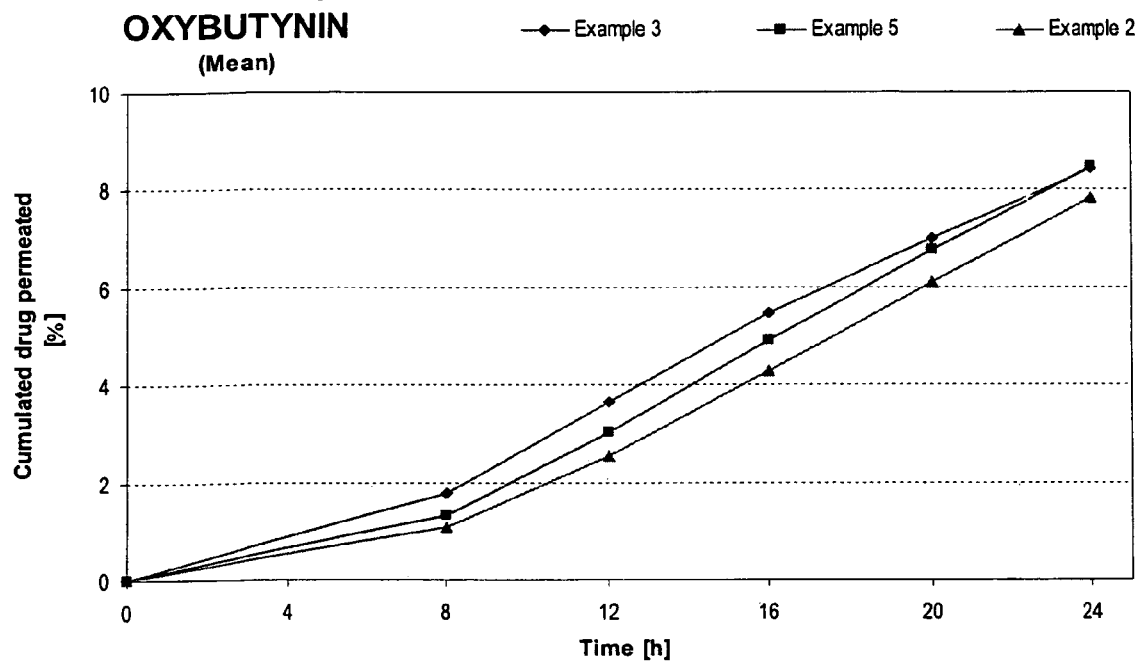
FIG. 4 is a graph illustrating the results of an in-vitro 24-hour comparative permeation study comparing permeation of a composition comprising oxybutynin, and a carrier, a composition comprising oxybutynin, urea and a carrier; and a composition comprising oxybutynin, urea, a carrier and additional solvents.
Figure 5:
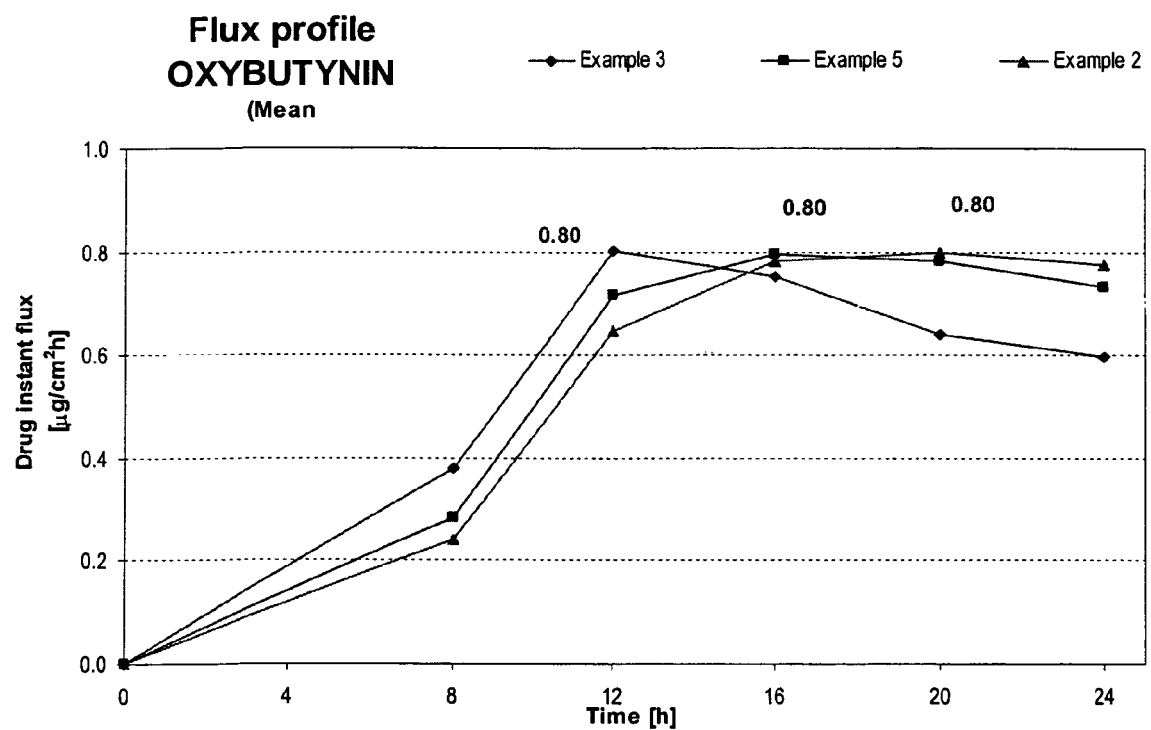
FIG. 5 is a graph illustrating the drug flux profiles of the compositions of FIG. 4.

Referring now to FIG. 4, the graph illustrates the results of a permeation study comparing Examples 3, 5, and 2, described above. The relative cumulated permeated amount of oxybutynin after 24 hours is similar for each example, i.e., approximately to 8%. Now referring to FIG. 5, although the three compositions present similar oxybutynin cumulated permeated amounts as shown in FIG. 4, FIG. 5 illustrates that Examples 3, 5, and 2, have similar maximal transdermal oxybutynin flux (close to 0.80 µg/cm$^2$h), but that the maximal transdermal oxybutynin flux is attained after 12 hours for Example 3, which contains no urea, and is attained after 16 hours for Example 5, and after 20 hours for Example 2, both of which comprise urea. Accordingly, both compositions comprising urea, Examples 2 and 5, have transdermal oxybutynin fluxes that were maintained over a longer period of time ("steady-state").

Pilot Pharmacokinetic Study of an Oxybutynin Gel Formulation in Healthy Volunteers A pilot study was conducted in Scope International (Hamburg, Germany) between Jan. 22 and Feb. 12, 2004 to determine Pharmacokinetics of oxybutynin and its metabolite, N-desethyloxybutynin. The study and its results are presented below.

Subjects and Methods

Healthy Caucasian females, aged 20 to 55, were recruited for the study. Subjects were required to have a body mass index of 20 to 28 kg/m² (weight in kilograms divided by the square of height in meters), to be non-smokers and to have no history of chronic medical illness or alcohol or drug abuse. Subjects were excluded on the basis of any preexisting condition or finding on the prestudy examination that would place them at risk during the study. Written informed consent was obtained from each subject before participating in any study-related procedures after discussion and explanation of the study.

Treatments were administered according to an open-label, multiple-dose, escalating dose titration pilot pharmacokinetic study and included a transdermal oxybutynin gel. Steady-state conditions were achieved by administering daily doses for 7 days. Subjects participated in 2 study periods during which the test medication (a transdermal gel) was applied once daily. 2 g of the gel (corresponding to a dose of 60 mg of oxybutynin) was applied daily during the first study period (Treatment A), then 1 g (corresponding to a dose of 30 mg of oxybutynin) during the second study period (Treatment B). A wash-out period of 7 days was observed between the two study periods. Both dosages were tested on same subjects. The design allows comparison between different dosages of the same formulation within the subject and removes inter-subject variability. The oxybutynin gels administered in this study comprised oxybutynin base 3.00% w/w, diethylene glycol monoethyl ether 2.50% w/w, propylene glycol 15.0% w/w, urea 5.00% w/w, ethanol 50.7% w/w, hydropropylcellulose KLUCEL HF 2.00% w/w, hydrochloric acid 0.1N 8.50% w/w, butylhydroxytoluene 0.05% w/w, and purified water qs.

The main objective of this study was to assess the pharnacokinetic parameters of an oxybutynin gel formulation, administered in two different doses, administering the product in 8 healthy female volunteers. Data on substances concentration at peak ($C_{max}$), time to reach peak ($t_{max}$) and area under the concentration/time curve (AUC) were calculated for both oxybutynin and N-desethyloxybutynin.

The secondary objective of this study was to record safety parameters such as adverse events, skin tolerance, vital signs, e.g., blood pressure and heart rate.

Pharmacokinetic Study Results

Figure 6:
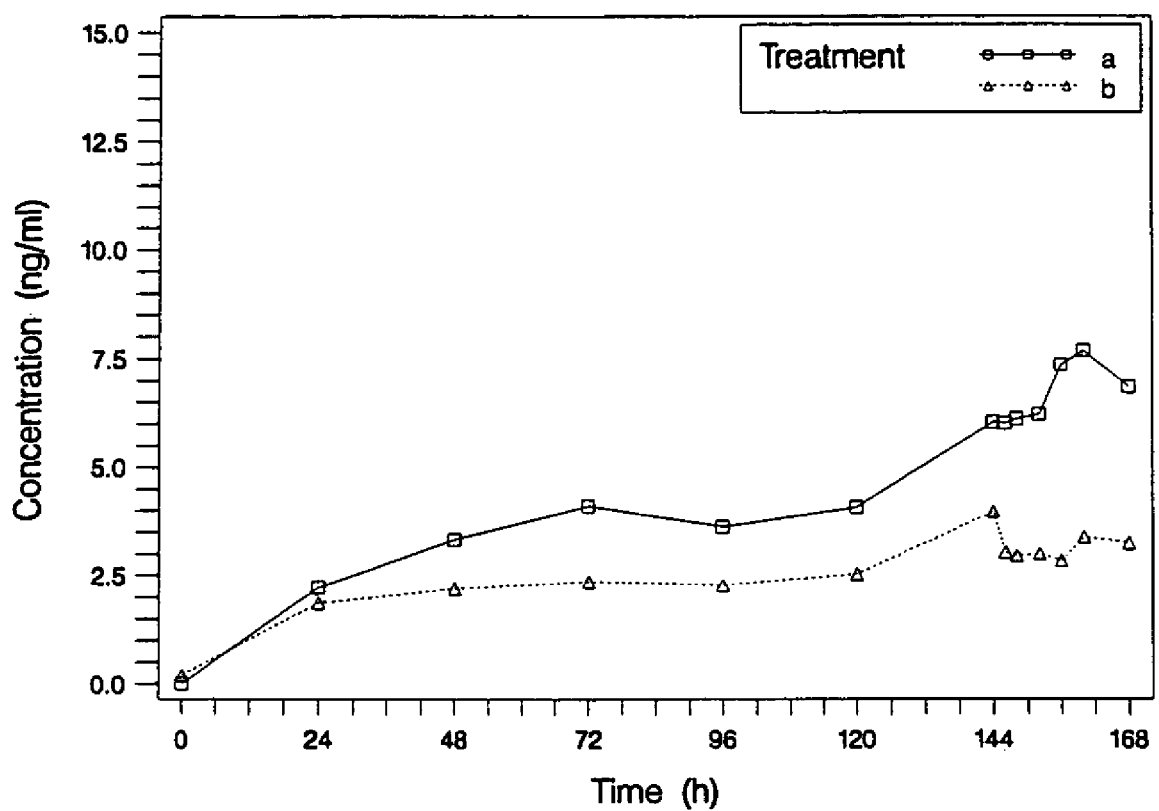
FIG. 6 is a graph illustrating the results of a pharmacokinetic study of the mean plasmatic oxybutynin concentrations in ng/ml over a 7-day period.

With reference to FIG. 6, the graph illustrates the mean oxybutynin plasma concentration profile from treatment A and treatment B. As can be seen between 24 hours and 168 hours, diminution of the oxybutynin dose by half, i.e., from 2 g to 1 g of gel, resulted in a 1.93-fold reduction (SD 1.08) of the mean oxybutynin plasmatic levels, i.e., from about 4.3 ng/ml (SD 2.6) to about 2.6 ng/ml (SD 1.9). As seen, an almost linear relationship between the applied oxybutynin dosage and the resulting oxybutynin plasmatic levels exists. In this regard, Tables 10, 11, and 12, infra, show the plasmatic ratios of oxybutynin: metabolite for treatments A and B, the plasmatic ratios of oxybutynin treatment A: oxybutynin treatment B, and the plasmatic ratios of metabolite treatment A to metabolite treatment B, respectively, taken at individual sampling times.

Figure 7:
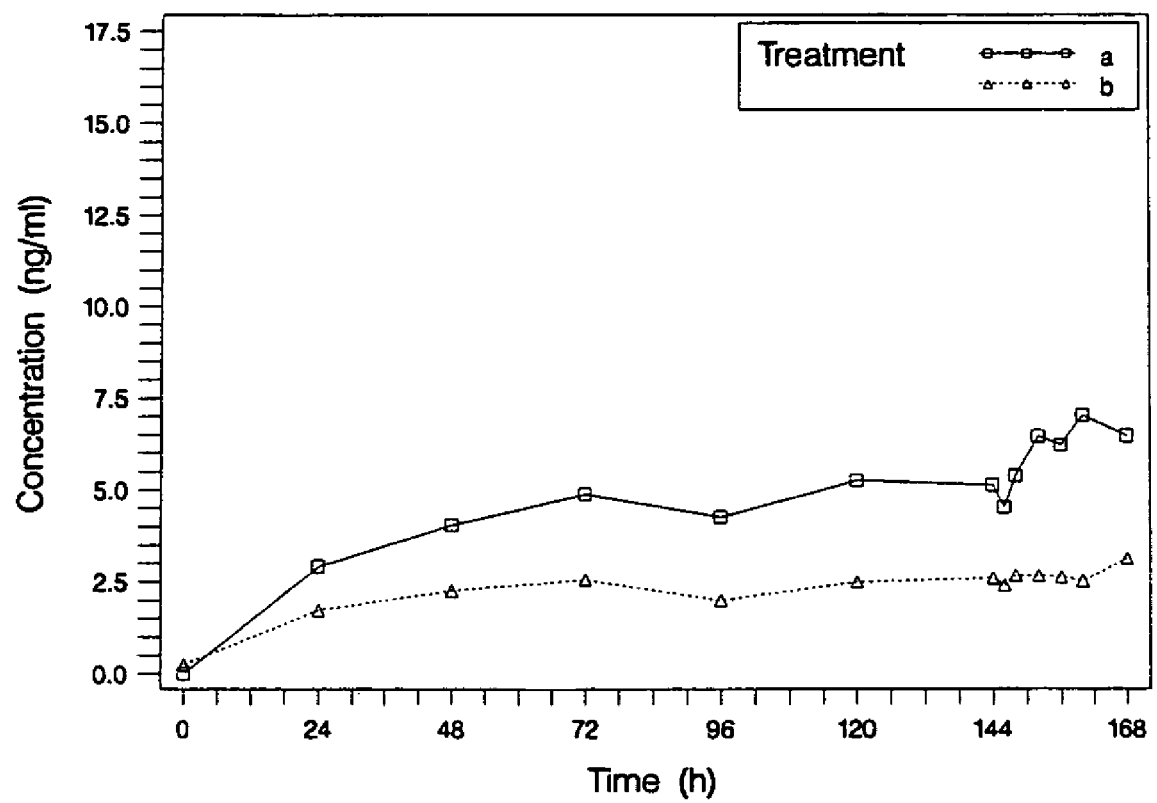
FIG. 7 is a graph illustrating the results of a pharmacokinetic study of mean plasmatic N-desethyloxybutynin concentrations in ng/ml over a 7-day period.

Referring now to FIG. 7, the graph illustrates the N-desethyloxybutynin plasma concentration profile from treatment A and treatment B. Similarly to FIG. 6, diminution of the oxybutynin dose by half, i.e., from 2 g to 1 g gel, resulted in a 2.06-fold reduction (SD 1.17) of mean N-desethyloxybutynin plasmatic levels, i.e., from about 4.7 ng/ml (SD 3.3) to about 2.4 ng/ml (SD 1.2). Thus, an almost linear relationship between oxybutynin dose applied and resulting N-desethyloxybutynin plasmatic levels exists.

The reduction of the daily dose of oxybutynin resulted in a lower variability of mean plasmatic oxybutynin and mean plasmatic N-desethyloxybutynin levels all through the duration of the studies (7 days each). It is also remarkable how outstandingly "flat" the profile of N-desethyloxybutynin obtained with treatment B (corresponding to a 30 mg daily dose of oxybutynin) is and how low the N-desethyloxybutynin mean plasmatic concentrations are. Consequently, the compositions and methods provide reduced incidences of oxybutynin-associated side effects, or provide lower-intensity oxybutynin-associated side effects.

Figure 8:
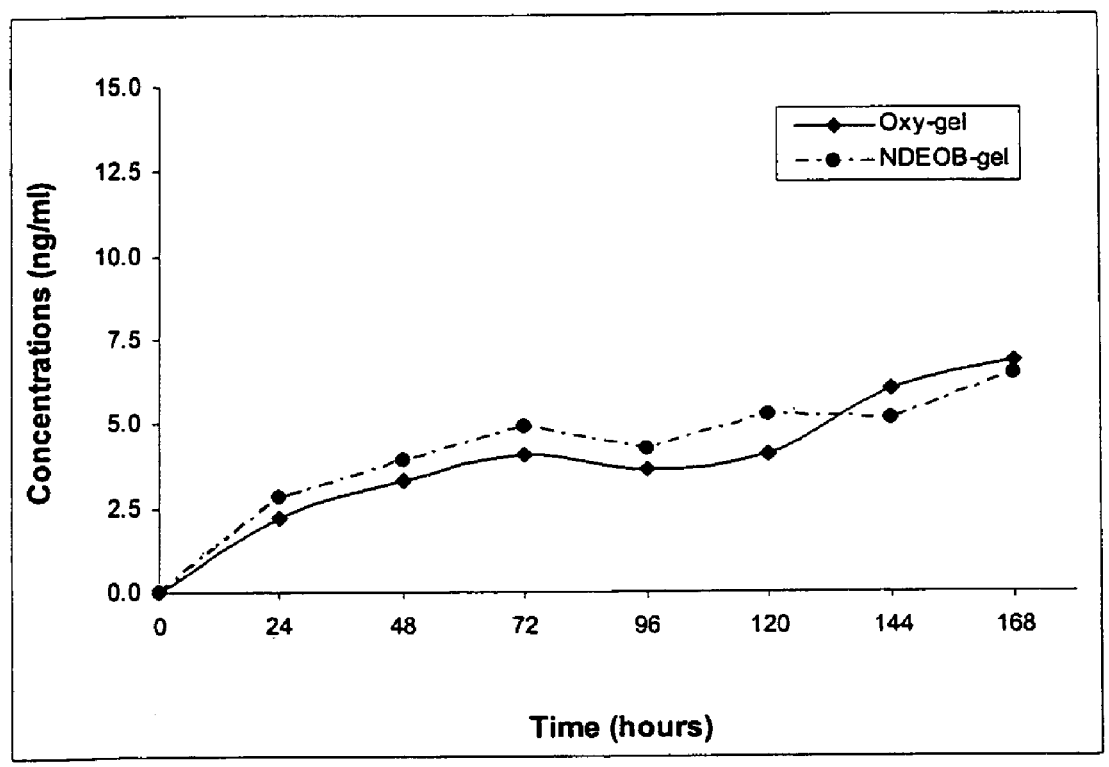
FIG. 8 is a graph illustrating the results from a pharmacokinetic study of the mean plasmatic Oxybutynin/N-desethyloxybutynin ratio over a 7-day period.

FIG. 8 shows the evolution of oxybutynin and N-desethyloxybutynin during treatment A. As illustrated in Tables 3 below, the ratio of mean oxybutynin plasmatic concentrations to mean plasmatic concentration of N-Desethyloxybutynin is constant and close to 1 (Mean 1.10; SD 0.67). In this regard, Tables 6 and 8, infra, show the oxybutynin concentrations for treatment A, and metabolite concentrations for treatment A, respectively, at individual sampling times.

TABLE 3

| Oxybutynin: N-Desethyloxybutynin mean plasmatic concentrations ratio (Treatment A) Scheduled time | | | | | | | |
|---|---|---|---|---|---|---|---|
| 0 | 24 | 48 | 72 | 96 | 120 | 144 | 168 |
| — | 0.85 | 0.98 | 0.96 | 0.99 | 0.91 | 1.54 | 1.49 |

Figure 9:
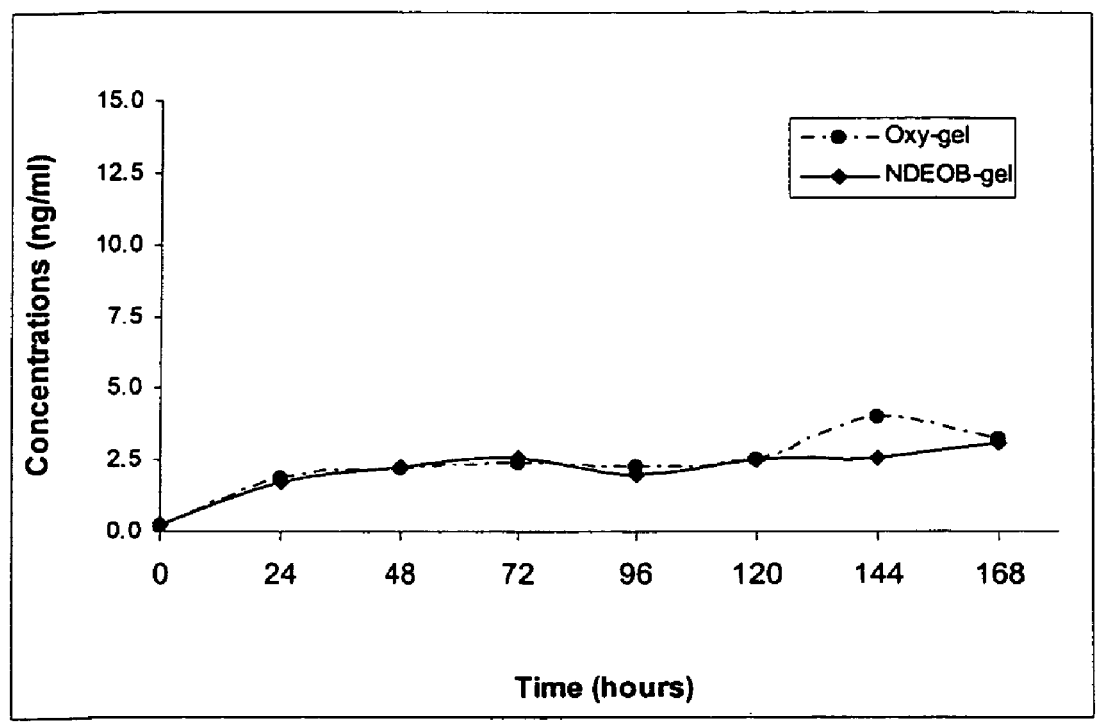
FIG. 9 is a graph illustrating the results of a pharmacokinetic study of mean plasmatic Oxybutynin/N-desethyloxybutynin ratio over a 7-day period.

With reference to FIG. 9, a graph demonstrates the evolution of oxybutynin and its metabolite, N-desethyloxybutynin during treatment B. Similarly to treatment A, and as shown in Tables 5 and 6, below, the ratio of mean oxybutynin plasmatic concentrations to mean plasmatic concentration of N-Desethyloxybutynin is constant and close to 1 (Mean 1.14; SD 0.57).

TABLE 4

| Oxybutynin: N-Desethyloxybutynin mean plasmatic concentrations ratio (Treatment B) Scheduled time | | | | | | | |
|---|---|---|---|---|---|---|---|
| 0 | 24 | 48 | 72 | 96 | 120 | 144 | 168 |
| — | 1.15 | 1.03 | 0.93 | 1.18 | 0.99 | 1.58 | 1.12 |

Accordingly, the reduction of the oxybutynin daily dose resulted in a higher and less variable ratio of mean oxybutynin to N-desethyloxybutynin mean plasmatic concentrations all through the duration of the studies (7 days each). In this regard, Tables 7 and 9, infra, show oxybutynin concentrations for treatment B, and metabolite concentrations for treatment B, respectively, at individual sampling times.

In conclusion, the obtained oxybutynin: N-desethyloxybutynin ratios were much higher for the oxybutynin gels administered in both treatments than the ratios associated with oral administration of oxybutynin. See, Zobrist et al, Mayo Clin Proc, Jun. 2003, Vol 78, which is incorporated herein by reference. Thus, the higher ratio provided by the transdermal administration are believed to be responsible for the fewer incidences of oxybutynin-associated side effects and/or for the lower-intensity oxybutynin-associated side effects.

Furthermore, the obtained oxybutynin: N-desethyloxybutynin ratios for the oxybutynin gels are comparable or even higher than the ratios obtained after administration of oxybutynin by a matrix-type transdermal system, as known in the art and as shown in Table 5 below. See, Zobrist et al, Mayo Clin Proc, June 2003, Vol 78, the content of which is incorporated herein by reference.

TABLE 5

| Estimated Oxybutynin: N-Desethyloxybutynin mean plasmatic concentrations ratio (OXYTROL ™ patch) Scheduled time (hours) | | | | | | | | | |
|---|---|---|---|---|---|---|---|---|---|
| 0 | 84 | 96 | 108 | 120 | 132 | 144 | 156 | 168 | 180 |
| — | 0.70 | 0.84 | 0.77 | 0.80 | 0.77 | 0.75 | 0.72 | 0.75 | 0.74 |

Comparative Permeation Studies

To illustrate the superior permeation effects of urea on oxybutynin, urea was compared to two known permeation enhancers for oxybutynin, namely, isopropyl myristate and lauric acid. The formulations are represented below.

| Composition | Example 7 | Example 8 | Example 9 |
|---|---|---|---|
| Oxybutynin base | 3.00 | 3.00 | 3.00 |
| Urea | 5.00 | — | — |
| Isopropyl Myristate | — | 5.00 | — |
| Lauric Acid | — | — | 5.00 |
| Hydroxypropyl cellulose | 2.00 | 2.00 | 2.00 |
| Hydrochloric acid 0.1 N | Q.S. pH 7.6 | Q.S. pH 7.2 | — |
| Triethanolamine | — | — | Q.S. pH 7.0 |
| Ethanol | 50.7 | 50.7 | 50.7 |
| Purified Water | Q.S. 100 | Q.S. 100 | Q.S. 100 |

Amounts are expressed as percent weight % w/w

Figure 10:
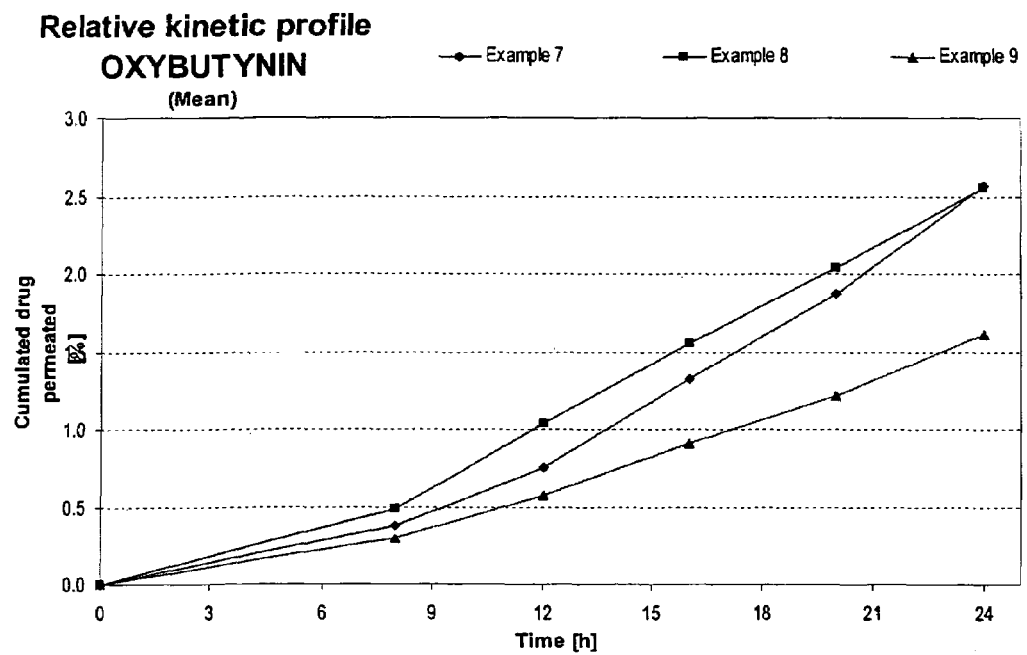
FIG. 10 is a graph illustrating the results of a comparative study comparing the absolute kinetic profile of a formulation comprising oxybutynin and urea, a formulation including oxybutynin and lauric acid, and a formulation including oxybutynin and isopropyl myristate.
Figure 11:
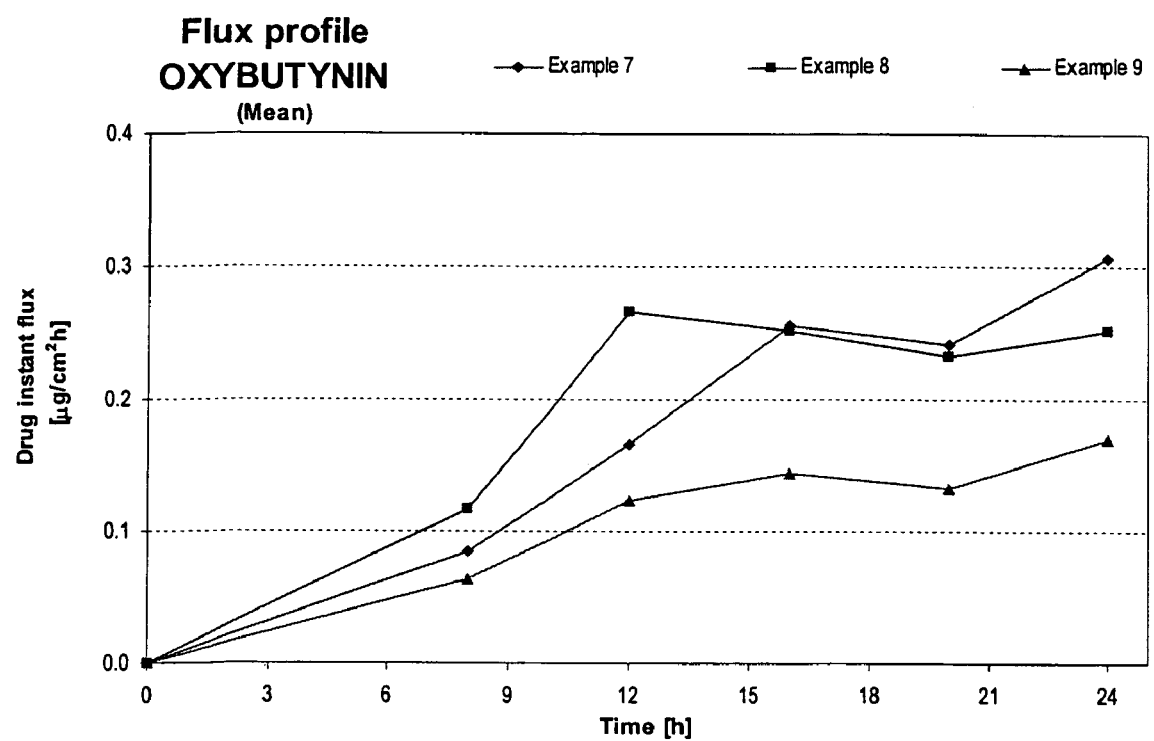
FIG. 11 is a graph illustrating the flux profile of the formulations of FIG. 10.

The results of the comparison study are shown in FIGS. 10 and 11. As illustrated by the graph in FIG. 10, the formulation containing urea enhances permeation of the oxybutynin as compared to lauric acid by 63%. Also illustrated in FIG. 10 is that the formulation containing isopropyl myristate exhibits cumulative oxybutynin permeation amounts similar to that of the urea formulation. However, the formulation containing the isopropyl myristate was found to be pharmaceutically undesirable due to instability of the formulation. The necessary amounts of the isopropyl myristate are difficult to dissolve in the hydroalcoholic vehicle of the invention. Accordingly, the isopropyl myristate exhibited a rapid and extensive phase separation, a phenomenon known as coalescence, within only hours.

As shown in FIG. 11, the flux profile graph indicates that the maximal flux is higher for the formulation containing urea than for the formulations containing lauric acid and isopropyl myristate by 80% and 22%, respectively. Further, the maximal flux is not reached after 24 hours for the lauric acid formulation, and is reached after 12 hours for the isopropyl myristate formulation. In sum, as illustrated by the higher permeation amounts and the higher maximal flux, urea is a superior permeation enhancer for oxybutynin than is lauric acid. Further, as illustrated by the higher maximal flux and the superior physical stability, urea is a superior permeation enhancer for oxybutynin that is isopropyl myristate.

The formulation in accordance with the present invention was also compared to two other formulations containing other known permeation enhancers, namely, triacetin and glycerol monooleate. The comparative formulations are represented below.

| Composition | Example 7 | Example 10 | Example 11 |
|---|---|---|---|
| Oxybutnin base | 3.00 | 3.00 | 3.00 |
| Urea | 5.00 | — | — |
| Triacetin | — | 5.00 | — |
| Glycerol monooleate | — | — | 5.00 |
| Hydroxypropyl cellulose | 2.00 | 2.00 | 2.00 |
| Hydrochloric acid 0.1 N | Q.S. pH 7.6 | Q.S. pH 7.2 | — |
| Triethanolamine | — | — | Q.S. pH 7.0 |
| Ethanol | 50.7 | 50.7 | 50.7 |
| Purified Water | Q.S. 100 | Q.S. 100 | Q.S. 100 |

Amounts are represented as percent weight by weight % w/w

Figure 12:
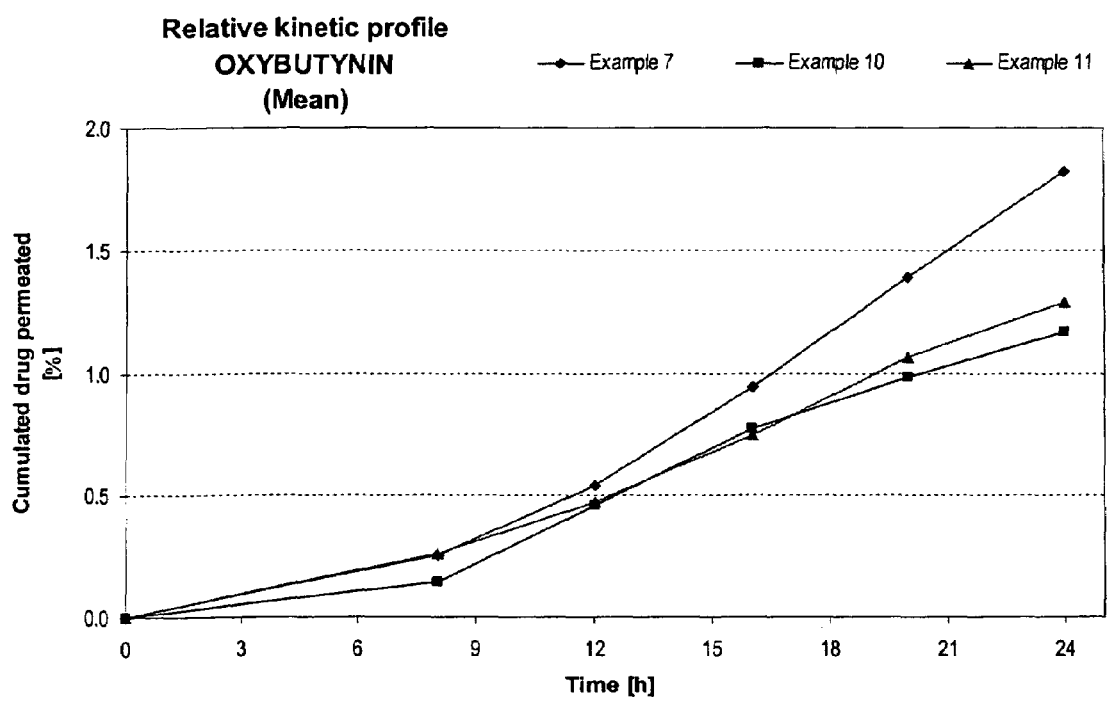
FIG. 12 is a graph illustrating the results of a comparative study comparing the absolute kinetic profile of a formulation including oxybutynin and urea, a formulation including oxybutynin and triacetin and a formulation including oxybutynin and glycerol monooleate.
Figure 13:
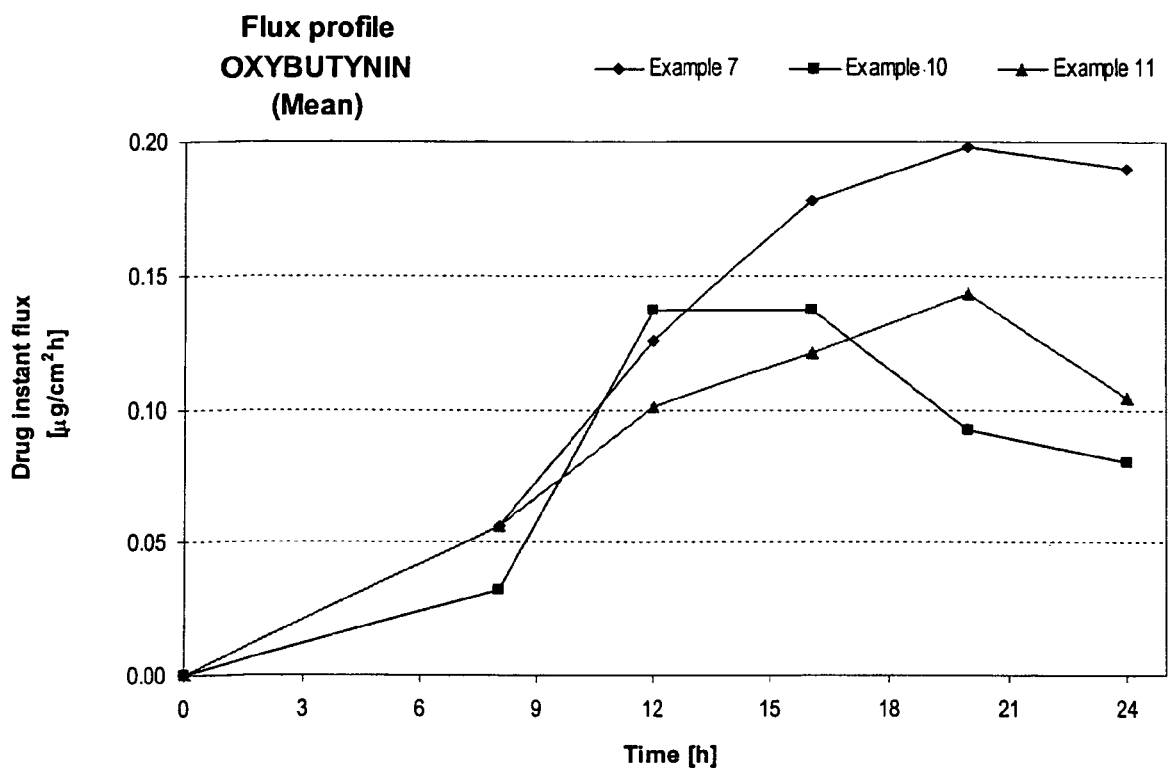
FIG. 13 is a graph illustrating the flux profile of the formulations of FIG. 12.

The results of this comparative study are shown in FIGS. 12 and 13. Referring to FIG. 12, the formulation containing urea has increased absolute transdermal absorption of oxybutynin as compared to the formulation containing triacetin and to the formulation containing glycerol monooleate, by 38% and 57%, respectively. The relative transdermal absorption after 24 hours is also increased for the formulation containing urea as compared to the formulation containing triacetin and the formulation containing glycerol monoolceate, by 41% and 56%, respectively.

Referring now to FIG. 13, the maximal and steady-state fluxes are also higher for the formulation containing urea. The steady-state flux for the formulation containing urea is 90% higher than the formulation containing triacetin and the formulation containing glycerol monooleate. Further, the maximum flux is reached at 20-hours, as for the glycerol monooleate, but 8-hours later than the formulation containing triacetin. As illustrated, the triacetin formulation reaches its maximum flux at 12-hours. This comparison shows that the oxybutynin sustained release potential is higher for formulations comprising urea than for formulations comprising glycerol monooleate since between 20 hours and 24-hours, the maximum flux decreases by 27% for glycerol monoolate (0.104 ug/cm$^2$h at 24 h vs. 0.143 ug/cm$^2$h at 20 h) and only by 4% for urea (0.190 ug/cm$^2$h at 24 h vs. 0.198 ug/cm$^2$h at 20 h). Thus, this study illustrates that urea is a better permeation enhancer than either glycerol monooleate or triacetin as demonstrated by the higher 24-hour cumulative oxybutynin permeated amounts and the higher maximal flux. Moreover, the formulation containing urea exhibits a sustained steady-state that might be responsible in vivo for lower variations in oxybutynin blood levels, and consequently for lower occurrences of undesirable side effects.

Figure 14:
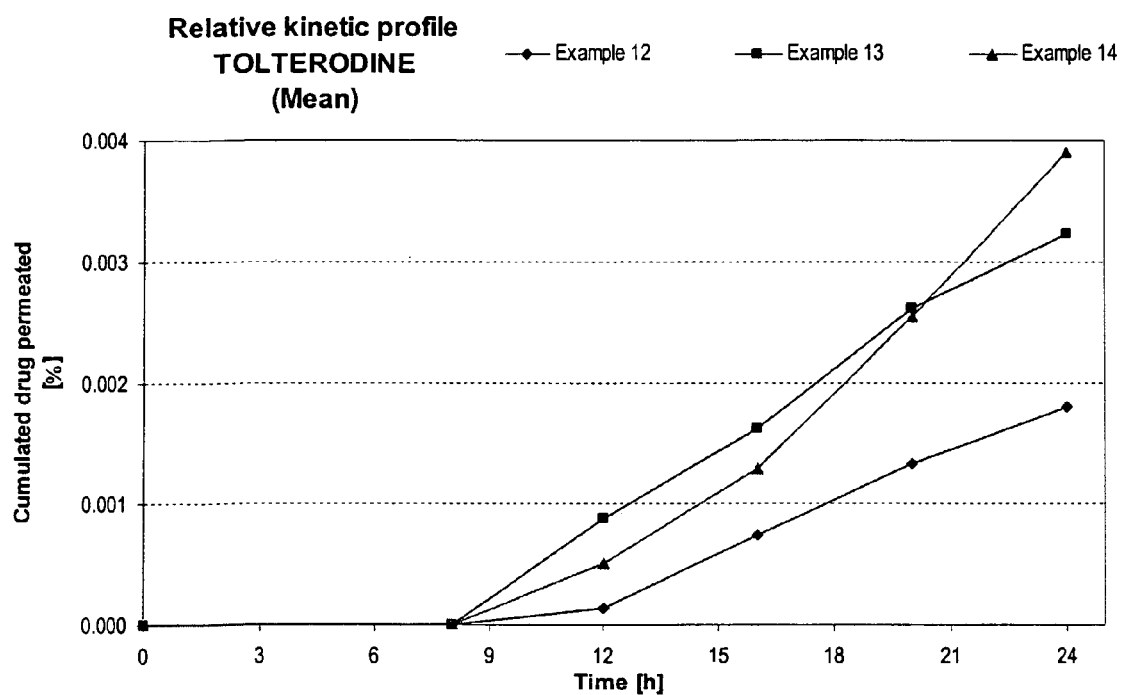
FIG. 14 is a graph illustrating the relative kinetic profile of a tolterodine formulation including urea as a permeation enhancer.

In addition to the superior permeation effects of urea for oxybutynin, FIG. 14 illustrates that the addition of urea, either alone or in the presence of other co-solvents, into a simple hydro-alcoholic formulation enhances the permeation of anticholinergic agents other than oxybutynin. In this study, the effects of urea as a permeation enhancer of tolterodine hydrogen tartrate was investigated. The comparative formulations are represented below.

| Composition | Example 12 | Example 13 | Example 14 |
|---|---|---|---|
| Tolterodine hydrogen tartrate base | 3.00 | 3.00 | 3.00 |
| Ethanol | 40.0 | 40.0 | 40.0 |
| Urea | — | 5.00 | 5.00 |
| Propylene glycol | — | — | 15.0 |
| Diethylene glycol monoethyl ether | — | — | 2.50 |
| Purified water | Q.S. 100 | Q.S. 100 | Q.S. 100 |

The results of the comparison study are shown in FIG. 14. As illustrated in FIG. 14, the formulation comprising urea enhances permeation of the tolterodine as compared to the reference formulation, which does not contain urea, by 85% after 24 hours. Additionally and as shown in FIG. 14, the formulation comprising urea and co-solvents, 2.5% diethylene glycol monoethyl ether and 15% propylene glycol, further increases skin permeation of tolterodine by 19%. Accordingly, this study demonstrates that the addition of urea alone or in the presence of co-solvents allows enhanced permeation to other anticholinergic agents.

Figure 15:
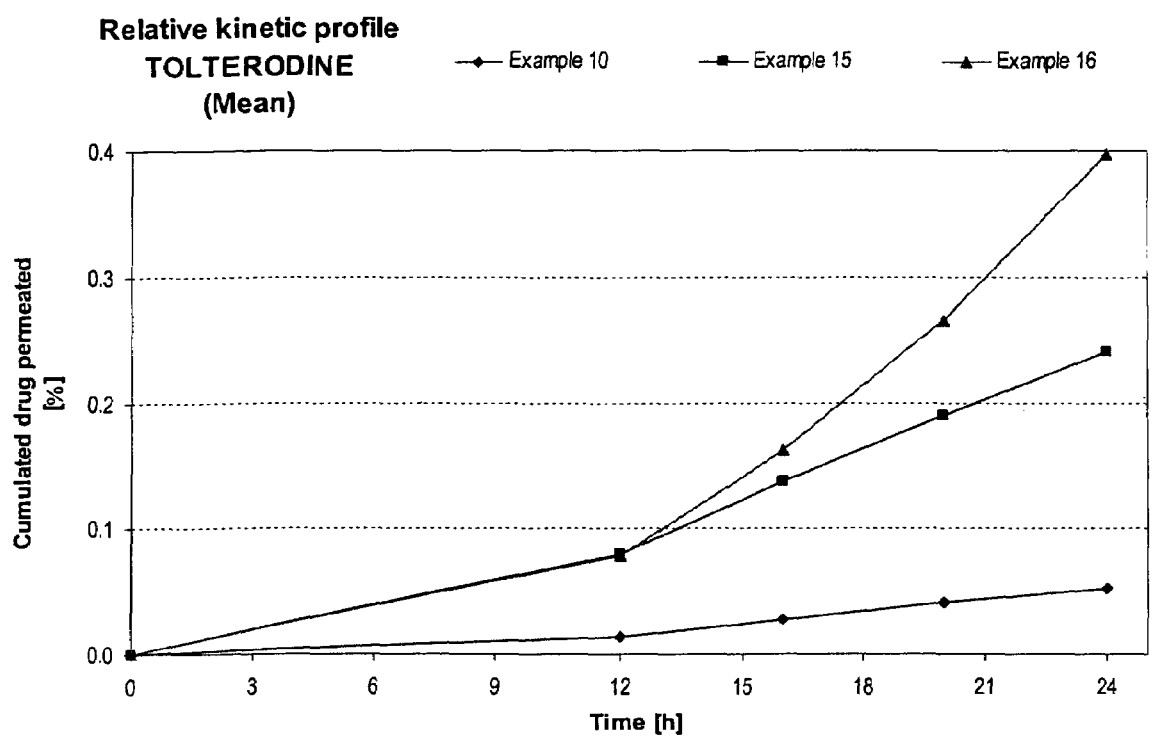
FIG. 15 is a graph illustrating the relative kinetic profile of tolterodine formulations including a urea derivative.

In addition to the superior permeation effects of urea on anticholinergic agents including oxybutynin and tolterodine, FIG. 15 illustrates that the addition of a urea-containing derivative, such as dimethyl urea, into a simple hydro-alcoholic formulation of tolterodine provides superior skin permeation of the drug. The comparative formulations are represented below.

| Composition | Example 10 | Example 15 | Example 16 |
|---|---|---|---|
| Tolterodine hydrogeno tartrate (expressed as a base) | 3.00 | 3.00 | 3.00 |
| Ethanol | 40.0 | 40.0 | 40.0 |
| Dimethylurea | — | 5.00 | 5.00 |
| Propylene glycol | — | — | 15.0 |
| Diethylene glycol monoethyl ether | — | — | 2.50 |
| Purified water | Q.S. 100 | Q.S. 100 | Q.S. 100 |

(Figures are expressed as percent weight by weight (w/w).)

Figure 16:
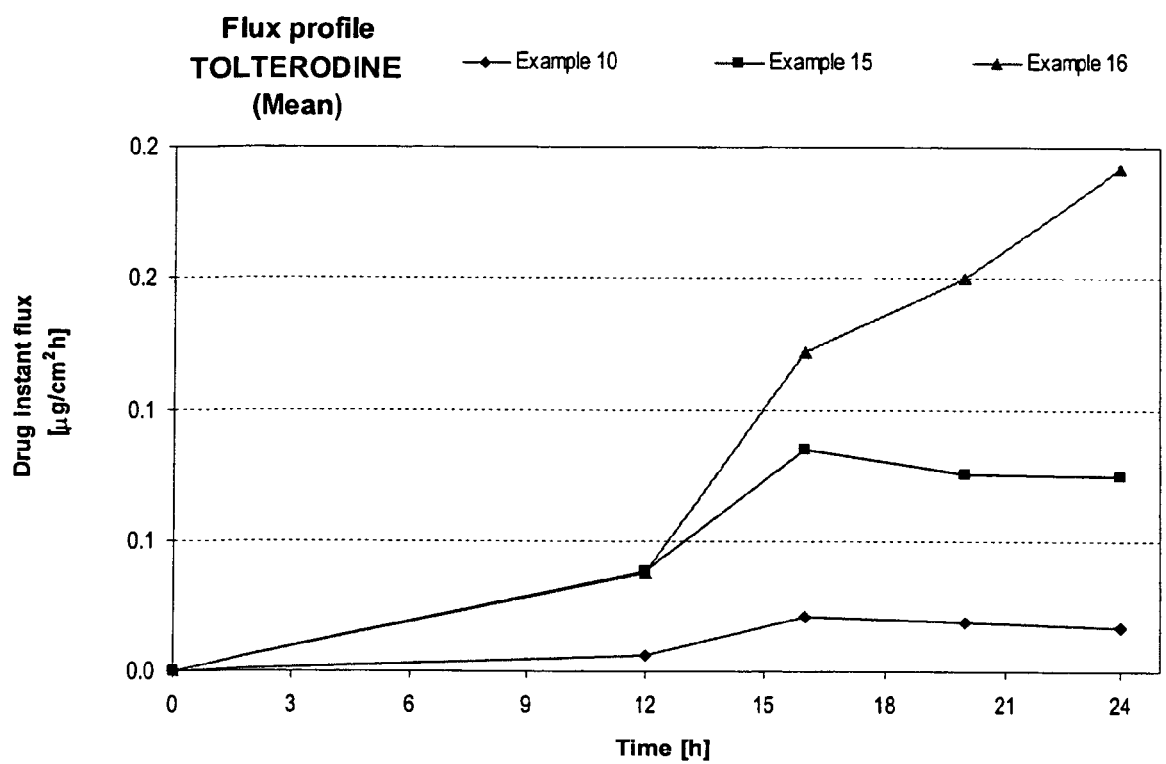
FIG. 16 is a graph illustrating the drug flux profile of the formulations of FIG. 15.

The results of the study are shown in FIGS. 15 and 16. Referring to FIG. 15, the formulation comprising tolterodine and dimethyl urea enhances permeation of the tolterodine by four times as compared to the reference formulation, Example 10, which does not contain dimethyl urea. Further, the formulation comprising dimethyl urea and co-solvents, propylene glycol and diethylene glycol monoethyl ether, (example 16) further enhances permeation of the drug by 7.7 times or 66%. Accordingly, this study demonstrates that urea containing derivatives such as dimethyl urea, either alone or in the presence of co-solvents, enhance permeation of anticholinergic agents.

Referring now to FIG. 16, the formulation comprising dimethyl urea enhances drug flux of tolterodine by 4 times as compared to the reference formulation. As shown, the steady state is achieved after 16 hours for each of the formulation comprising dimethyl urea and the reference formulation, example 10. However, the steady-state for the formulation comprising dimethyl urea and co-solvents is not achieved even after 24 hours. In sum, this comparative study illustrates the efficacy of urea derivatives as permeation enhancers for anticholinergic agents.

It is to be understood that the above-described examples are only illustrative of preferred embodiments of the present invention. Numerous modifications and alternative arrangements may be devised by those skilled in the art without departing from the spirit and scope of the present invention and the appended claims are intended to cover such modifications and arrangements.

TABLE 6

Oxybutynin - Concentrations by Sampling Times [ng/ml], Treatment A

| | Scheduled time [h] | | | | | | | | | | | | |
|---|---|---|---|---|---|---|---|---|---|---|---|---|---|
| Subject | 0 | 24 | 48 | 72 | 96 | 120 | 144 | 146 | 148 | 152 | 156 | 160 | 168 |
| 001 | 0.000 | 4.563 | 3.211 | 3.825 | 3.872 | 4.015 | 4.291 | 2.895 | 3.979 | 4.615 | 3.891 | 5.546 | 4.871 |
| 002 | 0.000 | 1.502 | 3.137 | 4.564 | 6.429 | 5.281 | 7.730 | 7.998 | 6.861 | 6.979 | 13.821 | 7.713 | 10.703 |
| 003 | 0.000 | 2.367 | 2.673 | 2.776 | 2.310 | 2.911 | 4.396 | 3.739 | 3.727 | 3.640 | 3.890 | 3.954 | 3.056 |
| 004 | 0.000 | 1.504 | 1.971 | 4.548 | 2.719 | 2.716 | 7.509 | 8.595 | 5.862 | 4.495 | 4.432 | 3.962 | 5.569 |
| 005 | 0.000 | 3.077 | 3.237 | 5.101 | 4.134 | 5.490 | 10.751 | 9.006 | 8.812 | 9.025 | 7.702 | 13.620 | 5.859 |
| 006 | 0.000 | 0.851 | 1.187 | 1.169 | 1.417 | 1.683 | 4.450 | 6.139 | 5.676 | 3.431 | 8.174 | 8.451 | 9.652 |
| 007 | 0.000 | 2.549 | 9.033 | 8.309 | 6.015 | 7.782 | 5.968 | 5.898 | 8.051 | 9.422 | 10.205 | 11.015 | 10.388 |
| 008 | 0.000 | 1.353 | 2.184 | 2.556 | 2.083 | 2.696 | 3.170 | 3.790 | 5.836 | 8.085 | 6.710 | 7.111 | 4.702 |
| N | 8 | 8 | 8 | 8 | 8 | 8 | 8 | 8 | 8 | 8 | 8 | 8 | 8 |
| Mean | 0.000 | 2.221 | 3.329 | 4.106 | 3.622 | 4.072 | 6.033 | 6.008 | 6.101 | 6.212 | 7.353 | 7.672 | 6.850 |
| SD | 0.000 | 1.196 | 2.413 | 2.136 | 1.840 | 2.001 | 2.500 | 2.373 | 1.780 | 2.454 | 3.458 | 3.372 | 2.946 |
| SE | 0.000 | 0.423 | 0.853 | 0.755 | 0.651 | 0.707 | 0.884 | 0.839 | 0.629 | 0.868 | 1.222 | 1.192 | 1.042 |
| CV | — | 53.8 | 72.5 | 52.0 | 50.8 | 49.1 | 41.4 | 39.5 | 29.2 | 39.5 | 47.0 | 44.0 | 43.0 |
| Min | 0.000 | 0.851 | 1.187 | 1.169 | 1.417 | 1.683 | 3.170 | 2.895 | 3.727 | 3.431 | 3.890 | 3.954 | 3.056 |
| Q1 | 0.000 | 1.428 | 2.078 | 2.666 | 2.197 | 2.706 | 4.344 | 3.765 | 4.828 | 4.068 | 4.162 | 4.754 | 4.787 |
| Med | 0.000 | 1.936 | 2.905 | 4.187 | 3.296 | 3.463 | 5.209 | 6.019 | 5.849 | 5.797 | 7.206 | 7.412 | 5.714 |
| Q3 | 0.000 | 2.813 | 3.224 | 4.833 | 5.075 | 5.386 | 7.620 | 8.297 | 7.456 | 8.555 | 9.190 | 9.733 | 10.020 |
| Max | 0.000 | 4.563 | 9.033 | 8.309 | 6.429 | 7.782 | 10.751 | 9.006 | 8.812 | 9.422 | 13.821 | 13.620 | 10.703 |
| GeoM | — | 1.963 | 2.822 | 3.595 | 3.217 | 3.664 | 5.617 | 5.565 | 5.866 | 5.778 | 6.687 | 7.041 | 6.290 |

TABLE 6-continued

Oxybutynin - Concentrations by Sampling Times [ng/ml], Treatment A

| Subject | Scheduled time [h] | | | | | | | | | | | | |
|---|---|---|---|---|---|---|---|---|---|---|---|---|---|
| | 0 | 24 | 48 | 72 | 96 | 120 | 144 | 146 | 148 | 152 | 156 | 160 | 168 |
| G_CV | — | 57.4 | 63.1 | 63.7 | 57.0 | 52.7 | 41.8 | 45.1 | 31.1 | 43.0 | 49.3 | 47.0 | 47.2 |
| N\|x > 0 | 0 | 8 | 8 | 8 | 8 | 8 | 8 | 8 | 8 | 8 | 8 | 8 | 8 |

TABLE 7

Oxybutynin - Concentrations by Sampling Times [ng/ml], Treatment B

| Subject | Scheduled time [h] | | | | | | | | | | | | |
|---|---|---|---|---|---|---|---|---|---|---|---|---|---|
| | 0 | 24 | 48 | 72 | 96 | 120 | 144 | 146 | 148 | 152 | 156 | 160 | 168 |
| 001 | 0.311 | 2.366 | 3.131 | 2.120 | 1.314 | 2.066 | 3.050 | 1.594 | 1.161 | 1.660 | 1.528 | 2.334 | 3.377 |
| 002 | 0.393 | 4.373 | 3.517 | 4.972 | 7.210 | 5.654 | 7.581 | 6.849 | 5.674 | 4.166 | 3.369 | 5.363 | 6.709 |
| 003 | 0.124 | 1.506 | 2.174 | 2.106 | 1.648 | 2.320 | 2.835 | 2.358 | 2.055 | 2.182 | 2.089 | 2.297 | 1.953 |
| 004 | 0.167 | 1.330 | 3.017 | 2.577 | 2.214 | 2.291 | 2.460 | 2.830 | 2.270 | 2.278 | 2.597 | 2.114 | 2.135 |
| 005 | 0.120 | 1.572 | 1.398 | 1.632 | 1.738 | 1.920 | 2.320 | 2.142 | 2.904 | 2.512 | 3.099 | 4.940 | 2.827 |
| 006 | 0.000 | 0.544 | 0.721 | 0.695 | 0.625 | 0.456 | 1.524 | 2.550 | 1.591 | 2.527 | 2.787 | 2.304 | 1.396 |
| 007 | 0.316 | 2.559 | 2.698 | 3.238 | 1.871 | 4.304 | 9.831 | 3.806 | 4.697 | 5.193 | 3.846 | 4.169 | 5.310 |
| 008 | 0.156 | 0.641 | 0.982 | 1.563 | 1.632 | 1.237 | 2.167 | 2.147 | 3.241 | 3.427 | 3.379 | 3.520 | 2.269 |
| N | 8 | 8 | 8 | 8 | 8 | 8 | 8 | 8 | 8 | 8 | 8 | 8 | 8 |
| Mean | 0.198 | 1.861 | 2.205 | 2.363 | 2.282 | 2.531 | 3.971 | 3.035 | 2.949 | 2.993 | 2.837 | 3.380 | 3.247 |
| SD | 0.130 | 1.240 | 1.058 | 1.293 | 2.045 | 1.672 | 3.018 | 1.671 | 1.552 | 1.183 | 0.756 | 1.311 | 1.841 |
| SE | 0.046 | 0.438 | 0.374 | 0.457 | 0.723 | 0.591 | 1.067 | 0.591 | 0.549 | 0.418 | 0.267 | 0.464 | 0.651 |
| CV | 65.5 | 66.6 | 48.0 | 54.7 | 89.6 | 66.1 | 76.0 | 55.1 | 52.6 | 39.5 | 26.6 | 38.8 | 56.7 |
| Min | 0.000 | 0.544 | 0.721 | 0.695 | 0.625 | 0.456 | 1.524 | 1.594 | 1.161 | 1.660 | 1.528 | 2.114 | 1.396 |
| Q1 | 0.122 | 0.986 | 1.190 | 1.598 | 1.473 | 1.579 | 2.244 | 2.145 | 1.823 | 2.230 | 2.343 | 2.301 | 2.044 |
| Med | 0.162 | 1.539 | 2.436 | 2.113 | 1.693 | 2.179 | 2.648 | 2.454 | 2.587 | 2.520 | 2.943 | 2.927 | 2.548 |
| Q3 | 0.314 | 2.463 | 3.074 | 2.908 | 2.043 | 3.312 | 5.316 | 3.318 | 3.969 | 3.797 | 3.374 | 4.555 | 4.344 |
| Max | 0.393 | 4.373 | 3.517 | 4.972 | 7.210 | 5.654 | 9.831 | 6.849 | 5.674 | 5.193 | 3.846 | 5.363 | 6.709 |
| GeoM | 0.205 | 1.524 | 1.930 | 2.063 | 1.809 | 2.031 | 3.240 | 2.748 | 2.611 | 2.810 | 2.735 | 3.168 | 2.861 |
| G_CV | 52.1 | 79.1 | 64.7 | 63.1 | 76.2 | 89.6 | 71.6 | 46.9 | 57.2 | 38.8 | 30.8 | 39.7 | 56.5 |
| N\|x > 0 | 7 | 8 | 8 | 8 | 8 | 8 | 8 | 8 | 8 | 8 | 8 | 8 | 8 |

TABLE 8

N-desethyloxybutynin - Concentrations by Sampling Times [ng/l], Treatment A

| Subject | Scheduled time [h] | | | | | | | | | | | | |
|---|---|---|---|---|---|---|---|---|---|---|---|---|---|
| | 0 | 24 | 48 | 72 | 96 | 120 | 144 | 146 | 148 | 152 | 156 | 160 | 168 |
| 001 | 0.000 | 3.696 | 3.518 | 3.431 | 3.808 | 4.468 | 3.134 | 2.726 | 3.628 | 3.941 | 3.722 | 4.657 | 4.648 |
| 002 | 0.000 | 1.125 | 1.834 | 2.466 | 2.671 | 2.666 | 4.161 | 3.722 | 3.615 | 2.973 | 3.118 | 3.536 | 4.227 |
| 003 | 0.000 | 2.837 | 3.429 | 3.243 | 2.248 | 2.953 | 3.394 | 3.268 | 3.810 | 3.868 | 3.602 | 3.557 | 3.054 |
| 004 | 0.000 | 1.600 | 2.163 | 3.861 | 3.090 | 3.511 | 2.945 | 2.677 | 3.405 | 2.821 | 3.584 | 3.727 | 2.940 |
| 005 | 0.000 | 5.777 | 5.987 | 8.922 | 7.899 | 10.113 | 14.054 | 10.792 | 11.670 | 13.675 | 11.970 | 12.339 | 10.263 |
| 006 | 0.000 | 1.260 | 1.020 | 1.430 | 1.580 | 1.943 | 1.502 | 1.284 | 1.983 | 3.284 | 3.214 | 2.571 | 2.676 |
| 007 | 0.000 | 3.563 | 10.561 | 10.645 | 8.230 | 10.092 | 7.071 | 6.375 | 9.418 | 12.810 | 12.501 | 16.846 | 16.480 |
| 008 | 0.000 | 3.433 | 3.800 | 5.055 | 4.478 | 6.246 | 4.707 | 5.295 | 5.487 | 8.173 | 7.990 | 8.998 | 7.438 |
| N | 8 | 8 | 8 | 8 | 8 | 8 | 8 | 8 | 8 | 8 | 8 | 8 | 8 |
| Mean | 0.000 | 2.911 | 4.039 | 4.882 | 4.251 | 5.249 | 5.121 | 4.517 | 5.377 | 6.443 | 6.213 | 7.029 | 6.466 |
| SD | 0.000 | 1.566 | 3.036 | 3.233 | 2.518 | 3.265 | 3.954 | 2.992 | 3.380 | 4.533 | 4.042 | 5.198 | 4.817 |
| SE | 0.000 | 0.554 | 1.073 | 1.143 | 0.890 | 1.154 | 1.398 | 1.058 | 1.195 | 1.603 | 1.429 | 1.838 | 1.703 |
| CV | — | 53.8 | 75.2 | 66.2 | 59.2 | 62.2 | 77.2 | 66.2 | 62.9 | 70.4 | 65.1 | 73.9 | 74.5 |
| Min | 0.000 | 1.125 | 1.020 | 1.430 | 1.580 | 1.943 | 1.502 | 1.284 | 1.983 | 2.821 | 3.118 | 2.571 | 2.676 |
| Q1 | 0.000 | 1.430 | 1.999 | 2.855 | 2.460 | 2.810 | 3.040 | 2.702 | 3.510 | 3.129 | 3.399 | 3.547 | 2.997 |
| Med | 0.000 | 3.135 | 3.474 | 3.646 | 3.449 | 3.990 | 3.778 | 3.495 | 3.719 | 3.905 | 3.662 | 4.192 | 4.438 |
| Q3 | 0.000 | 3.630 | 4.894 | 6.989 | 6.189 | 8.169 | 5.889 | 5.835 | 7.453 | 10.492 | 9.980 | 10.669 | 8.851 |
| Max | 0.000 | 5.777 | 10.561 | 10.645 | 8.230 | 10.113 | 14.054 | 10.792 | 11.670 | 13.675 | 12.501 | 16.846 | 16.480 |
| GeoM | — | 2.530 | 3.226 | 4.052 | 3.664 | 4.447 | 4.171 | 3.778 | 4.609 | 5.277 | 5.248 | 5.658 | 5.269 |
| G_CV | — | 64.0 | 82.5 | 73.4 | 63.3 | 67.6 | 74.0 | 71.7 | 63.3 | 73.3 | 65.9 | 77.4 | 73.5 |
| N\|x > 0 | 0 | 8 | 8 | 8 | 8 | 8 | 8 | 8 | 8 | 8 | 8 | 8 | 8 |

TABLE 9

N-desethyloxybutynin - Concentrations by Sampling Times [ng/l], Treatment B

| Subject | Scheduled time [h] | | | | | | | | | | | | |
|---|---|---|---|---|---|---|---|---|---|---|---|---|---|
| | 0 | 24 | 48 | 72 | 96 | 120 | 144 | 146 | 148 | 152 | 156 | 160 | 168 |
| 001 | 0.284 | 1.944 | 1.892 | 2.099 | 0.698 | 1.538 | 1.843 | 1.637 | 1.307 | 1.354 | 1.692 | 1.743 | 1.930 |
| 002 | 0.375 | 1.532 | 2.071 | 3.072 | 2.844 | 3.215 | 3.184 | 2.907 | 2.548 | 2.279 | 2.224 | 1.910 | 3.017 |
| 003 | 0.105 | 1.540 | 2.168 | 2.672 | 1.928 | 2.805 | 2.538 | 2.596 | 2.811 | 2.603 | 2.939 | 2.208 | 2.339 |
| 004 | 0.213 | 1.000 | 3.402 | 2.445 | 2.395 | 2.385 | 2.555 | 2.282 | 2.471 | 2.130 | 1.788 | 1.928 | 2.530 |
| 005 | 0.188 | 2.393 | 2.618 | 1.996 | 1.781 | 2.346 | 2.172 | 1.962 | 2.430 | 2.470 | 2.924 | 2.805 | 3.410 |
| 006 | 0.000 | 0.576 | 0.643 | 0.821 | 0.611 | 0.583 | 0.574 | 0.440 | 0.809 | 1.058 | 0.960 | 0.875 | 1.327 |
| 007 | 0.489 | 3.610 | 3.363 | 4.480 | 2.729 | 4.306 | 5.240 | 4.918 | 5.453 | 5.125 | 3.887 | 4.413 | 6.614 |
| 008 | 0.335 | 1.200 | 1.913 | 2.822 | 2.951 | 2.702 | 2.664 | 2.440 | 3.458 | 4.268 | 4.571 | 4.285 | 3.762 |
| N | 8 | 8 | 8 | 8 | 8 | 8 | 8 | 8 | 8 | 8 | 8 | 8 | 8 |
| Mean | 0.249 | 1.724 | 2.259 | 2.551 | 1.992 | 2.485 | 2.596 | 2.398 | 2.661 | 2.661 | 2.623 | 2.521 | 3.116 |
| SD | 0.156 | 0.944 | 0.892 | 1.042 | 0.924 | 1.105 | 1.319 | 1.269 | 1.405 | 1.384 | 1.200 | 1.248 | 1.617 |
| SE | 0.055 | 0.334 | 0.315 | 0.368 | 0.327 | 0.391 | 0.466 | 0.449 | 0.497 | 0.489 | 0.424 | 0.441 | 0.572 |
| CV | 62.7 | 54.8 | 39.5 | 40.8 | 46.4 | 44.5 | 50.8 | 52.9 | 52.8 | 52.0 | 45.7 | 49.5 | 51.9 |
| Min | 0.000 | 0.576 | 0.643 | 0.821 | 0.611 | 0.583 | 0.574 | 0.440 | 0.809 | 1.058 | 0.960 | 0.875 | 1.327 |
| Q1 | 0.147 | 1.100 | 1.903 | 2.048 | 1.240 | 1.942 | 2.008 | 1.800 | 1.869 | 1.742 | 1.740 | 1.827 | 2.135 |
| Med | 0.249 | 1.536 | 2.120 | 2.559 | 2.162 | 2.544 | 2.547 | 2.361 | 2.510 | 2.375 | 2.574 | 2.068 | 2.774 |
| Q3 | 0.355 | 2.169 | 2.991 | 2.947 | 2.787 | 3.010 | 2.924 | 2.752 | 3.135 | 3.436 | 3.413 | 3.545 | 3.586 |
| Max | 0.489 | 3.610 | 3.402 | 4.480 | 2.951 | 4.306 | 5.240 | 4.918 | 5.453 | 5.125 | 4.571 | 4.413 | 6.614 |
| GeoM | 0.257 | 1.512 | 2.051 | 2.331 | 1.730 | 2.189 | 2.252 | 2.033 | 2.326 | 2.365 | 2.367 | 2.250 | 2.809 |
| G_CV | 54.7 | 60.6 | 56.2 | 52.2 | 69.6 | 67.0 | 70.2 | 79.2 | 63.6 | 56.3 | 53.8 | 56.3 | 50.8 |
| N\|x > 0 | 7 | 8 | 8 | 8 | 8 | 8 | 8 | 8 | 8 | 8 | 8 | 8 | 8 |

TABLE 10

Oxybutynin: N-desethyloxybutynin - Ratios by Sampling Times

Oxybutynin/N-Desethyloxybutynin ratio (Treatment A)

| subject | Scheduled time | | | | | | | | | |
|---|---|---|---|---|---|---|---|---|---|---|
| | 0 | 24 | 48 | 72 | 96 | 120 | 144 | 168 | | |
| 1 | #DIV/0! | 1.234578 | 1.275218 | 1.114835 | 1.016807 | 0.898612 | 1.369177 | 1.047978 | | |
| 2 | #DIV/0! | 1.335111 | 1.710469 | 1.85077 | 2.406964 | 1.98087 | 1.857727 | 2.532056 | | |
| 3 | #DIV/0! | 0.834332 | 0.779528 | 0.855998 | 1.02758 | 0.985777 | 1.295227 | 1.000655 | | |
| 4 | #DIV/0! | 0.94 | 0.911234 | 1.177933 | 0.879935 | 0.773569 | 2.549745 | 1.894218 | | |
| 5 | #DIV/0! | 0.532629 | 0.540671 | 0.571733 | 0.523357 | 0.542866 | 0.764978 | 0.570886 | | |
| 6 | #DIV/0! | 0.675397 | 1.163725 | 0.817483 | 0.896835 | 0.866186 | 2.962716 | 3.606876 | | |
| 7 | #DIV/0! | 0.715408 | 0.855317 | 0.780554 | 0.730863 | 0.771106 | 0.844011 | 0.63034 | | |
| 8 | #DIV/0! | 0.556104 | 0.574737 | 0.505638 | 0.465163 | 0.431636 | 0.673465 | 0.632159 | | |
| mean | #DIV/0! | 0.85 | 0.98 | 0.96 | 0.99 | 0.91 | 1.54 | 1.49 | Mean | 1.10 |
| SD | #DIV/0! | 0.30 | 0.39 | 0.43 | 0.61 | 0.47 | 0.85 | 1.10 | SD | 0.67 |
| RSD | #DIV/0! | 35.1 | 40.1 | 44.7 | 61.2 | 52.0 | 55.3 | 73.9 | RSD | 60.7 |

| Oxy-butynin subject | Oxybutynin/N-Desethyloxybutynin ratio (Treatment B) Scheduled time | | | | | | | | | |
|---|---|---|---|---|---|---|---|---|---|---|
| | 0 | 24 | 48 | 72 | 96 | 120 | 144 | 168 | | |
| 1 | 1.09507 | 1.217078 | 1.654863 | 1.010005 | 1.882521 | 1.343303 | 1.65491 | 1.749741 | | |
| 2 | 1.048 | 2.854439 | 1.698213 | 1.61849 | 2.535162 | 1.758631 | 2.465766 | 2.223732 | | |
| 3 | 1.180952 | 0.977922 | 1.002768 | 0.788174 | 0.854772 | 0.827094 | 1.117021 | 0.834972 | | |
| 4 | 0.784038 | 1.33 | 0.886831 | 1.053988 | 0.924426 | 0.960587 | 0.962818 | 0.843874 | | |
| 5 | 0.638298 | 0.656916 | 0.533995 | 0.817635 | 0.975856 | 0.818414 | 1.06814 | 0.829032 | | |
| 6 | #DIV/0! | 0.944444 | 1.121306 | 0.846529 | 1.022913 | 0.782161 | 2.655052 | 1.051997 | | |
| 7 | 0.646217 | 0.708864 | 0.80226 | 0.722768 | 0.685599 | 0.999536 | 1.876145 | 0.802842 | | |
| 8 | 0.465672 | 0.534167 | 0.51333 | 0.553863 | 0.553033 | 0.457809 | 0.813438 | 0.603137 | | |
| mean | #DIV/0! | 1.15 | 1.03 | 0.93 | 1.18 | 0.99 | 1.58 | 1.12 | Mean | 1.14 |
| SD | #DIV/0! | 0.74 | 0.45 | 0.32 | 0.68 | 0.40 | 0.70 | 0.56 | SD | 0.57 |
| RSD | #DIV/0! | 64.2 | 44.0 | 34.6 | 57.4 | 39.9 | 44.7 | 50.5 | RSD | 50.5 |

TABLE 11

Oxybutynin - Treatment A:Treatment B Ratios by Sampling Times
Treatment A/Treatment B Ratio - Oxybutynin

| subject | \multicolumn{8}{c}{Scheduled time} | | | |
|---|---|---|---|---|---|---|---|---|---|---|
| | 0 | 24 | 48 | 72 | 96 | 120 | 144 | 168 | | |
| 1 | 0 | 1.92857 | 1.02555 | 1.80425 | 2.94673 | 1.94337 | 1.40689 | 1.4424 | | |
| 2 | 0 | 0.34347 | 0.89195 | 0.91794 | 0.89168 | 0.93403 | 0.98459 | 1.59532 | | |
| 3 | 0 | 1.57171 | 1.22953 | 1.31814 | 1.4017 | 1.25474 | 1.55062 | 1.56477 | | |
| 4 | 0 | 1.13083 | 0.6533 | 1.76484 | 1.22809 | 1.18551 | 3.05244 | 2.60843 | | |
| 5 | 0 | 1.95738 | 2.31545 | 3.12561 | 2.3786 | 2.85938 | 4.63405 | 2.07252 | | |
| 6 | #DIV/0! | 1.56434 | 1.64632 | 1.68201 | 2.2672 | 3.69079 | 2.91995 | 6.91404 | | |
| 7 | 0 | 0.99609 | 3.34804 | 2.56609 | 3.21486 | 1.80809 | 0.60706 | 1.95631 | | |
| 8 | 0 | 2.11076 | 2.22403 | 1.63532 | 1.27635 | 2.17947 | 1.46285 | 2.07228 | | |
| mean | #DIV/0! | 1.45 | 1.67 | 1.85 | 1.95 | 1.98 | 2.08 | 2.53 | Mean | 1.93 |
| SD | #DIV/0! | 0.60 | 0.91 | 0.69 | 0.87 | 0.93 | 1.34 | 1.81 | SD | 1.08 |
| RSD | #DIV/0! | 41.1 | 54.6 | 37.5 | 44.5 | 46.8 | 64.7 | 71.6 | RSD | 55.9 |

TABLE 12

N-desethyloxybutynin - Treatment A:Treatment B Ratios by Sampling Times
Treatment A/Treatment B Ratio - N-Desethyloxybutynin

| subject | \multicolumn{8}{c}{Scheduled time} | | | |
|---|---|---|---|---|---|---|---|---|---|---|
| | 192 | 216 | 240 | 264 | 288 | 312 | 336 | 360 | | |
| 1 | 0 | 1.9012 | 1.3309 | 1.6346 | 5.45559 | 2.90507 | 1.70049 | 2.40829 | | |
| 2 | 0 | 0.7343 | 0.8856 | 0.8027 | 0.93917 | 0.82924 | 1.30685 | 1.40106 | | |
| 3 | 0 | 1.8422 | 1.5816 | 1.2137 | 1.16598 | 1.05276 | 1.33727 | 1.30569 | | |
| 4 | 0 | 1.6 | 0.6358 | 1.5791 | 1.29019 | 1.47212 | 1.15264 | 1.16206 | | |
| 5 | 0 | 2.4141 | 2.2869 | 4.4699 | 4.43515 | 4.31074 | 6.47053 | 3.00968 | | |
| 6 | ##### | 2.1875 | 1.5863 | 1.7418 | 2.58592 | 3.33276 | 2.61672 | 2.01658 | | |
| 7 | 0 | 0.987 | 3.1404 | 2.3761 | 3.01576 | 2.34371 | 1.34943 | 2.49168 | | |
| 8 | 0 | 2.0275 | 1.9864 | 1.7913 | 1.51745 | 2.31162 | 1.76689 | 1.97714 | | |
| mean | ##### | 1.71 | 1.68 | 1.95 | 2.55 | 2.32 | 2.21 | 1.97 | Mean | 2.06 |
| SD | ##### | 0.58 | 0.80 | 1.11 | 1.66 | 1.19 | 1.78 | 0.65 | SD | 1.17 |
| RSD | ##### | 34.0 | 47.5 | 57.1 | 65.2 | 51.2 | 80.5 | 33.0 | RSD | 56.7 |

While the invention has been described and pointed out in detail with reference to operative embodiments thereof, it will be understood by those skilled in the art that various changes, modifications, substitutions, and omissions can be made without departing from the spirit of the invention. It is intended therefore, that the invention embrace those equivalents within the scope of the claims that follow.

What is claimed is:

1. A non-occlusive composition for topical or transdermal administration of an anticholinergic or antispasmodic agent, the composition comprising:

at least one anticholinergic or antispasmodic agent of at least one of oxybutynin, flavoxate, imipramine, propantheline, phenylpropanolamine, darifenacin, duloxetine, tolterodine tartrate, trospium, or solifenacin succinate or a pharmaceutically acceptable salt thereof in an amount between about 0.1 to 20% by weight of the formulation;

a compound selected from the group consisting of urea, 1,3-dimethylurea, 1,1-diethylurea, 1-acetyl-1-phenylurea, isopropylideneurea, allophanic acid, hydantoic acid, allophanoyl, pyrrolidone carboxylic acid, biuret, thiobiuret, dithiobiuret, triuret and 2-(3-methylureido)-1-naphthoic acid in an amount of between about 1 to 20% by weight of the formulation for enhancing permeation of the anticholinergic or antispasmodic agent; and a carrier suitable for transdermal or topical administration and comprising the combination of an alcohol, a polyalcohol, and either a monoalkyl ether of diethylene glycol or a tetraglycol furol present in the carrier in a combined amount effective with the amount of urea-containing compound to enhance permeation of the anticholinergic or antispasmodic agent through dermal or mucosal surfaces;

wherein the alcohol is present in an amount of about 30 to 70% by weight of the formulation, the polyalcohol is present in an amount of about 1 to 15% by weight of the formulation, and the monoalkyl ether of diethylene glycol or tetraglycol furol is present in an amount between about 1 to 15% by weight of the formulation.

2. The composition of claim 1, wherein the anticholinergic or antispasmodic agent is oxybutynin, oxybutynin free base, or a pharmaceutically acceptable salt thereof, the urea-containing compound is urea, the alcohol is ethanol, propanol, isopropanol, 1-butanol, 2-butanol or a mixture thereof, the polyalcohol is propylene glycol, dipropylene glycol or a mixture of thereof; the monoalkyl ether of diethylene glycol, when present, is diethylene glycol monomethyl ether, diethylene glycol monoethyl ether or a mixture thereof, and the tetraglycol, when present, is glycofurol.

3. The composition of claim 2, wherein the oxybutynin is as a racemate or an isomer.

4. The composition of claim 2, wherein the pharmaceutically acceptable salt of oxybutynin is selected from the group consisting of acetate, bitartrate, citrate, edetate, edisylate, estolate, esylate, fumarate, gluceptate, gluconate, glutamate, hydrobromide, hydrochloride, lactate, malate, maleate, mandelate, mesylate, methylnitrate, mucate, napsylate, nitrate, pamoate, pantothenate, phosphate, salicylate, stearate, succinate, sulfate, tannate and tartrate.

5. The composition of claim 2, wherein the composition provides a steady plasma concentration of oxybutynin to a subject administered with the composition.

6. The composition of claim 1, further comprising a gelling agent, solvent, antimicrobial agent, preservative, antioxidant, buffer, humectant, sequestering agent, moisturizer, emollient, or additional permeation enhancer.

7. The composition of claim 1, wherein the composition is in the form of an ointment, cream, gel, foam, lotion, liposome, micelle, microsphere, lacquer, non occlusive dressing or a combination thereof.

8. A non-occlusive composition for topical or transdermal administration of oxybutynin, the composition comprising:
  oxybutynin, oxybutynin free base or a pharmaceutically acceptable salt of oxybutynin present in an amount between about 1 to 5% by weight of the formulation;
  a compound selected from the group consisting of urea, 1,3-dimethylurea, 1,1-diethylurea, 1-acetyl-1-phenylurea, isopropylideneurea, allophanic acid, hydantoic acid, allophanoyl, pyrrolidone carboxylic acid, biuret, thiobiuret, dithiobiuret, triuret and 2-(3-methylureido)-1-naphthoic acid present in an amount between about 1 to 10% by weight of the formulation; and
  a carrier present in an amount between about 40 to 80 percent by weight of the formulation, wherein the carrier comprises the combination of an alcohol, a polyalcohol, water and a monoalkyl ether of diethylene glycol or a tetraglycol furol,
  wherein the alcohol is present in an amount of about 30 to 70% by weight of the formulation, the polyalcohol is present in an amount of about 1 to 15% by weight of the formulation, and the monoalkyl ether of diethylene glycol or tetraglycol furol is present in an amount of about 1 to 1500 by weight of the formulation.

9. The composition of claim 8, wherein the composition further includes a gelling agent present in an amount of about 1 to 10%, the alcohol is ethanol, propanol, isopropanol, 1-butanol, 2-butanol or a mixture thereof, the polyalcohol is propylene glycol, dipropylene glycol or a mixture of thereof the monoalkyl ether of diethylene glycol, when present, is diethylene glycol monomethyl ether, diethylene glycol monoethyl ether or a mixture thereof, and the tetraglycol, when present, is glycofurol.

10. A method for treating overactive bladder or urge and urinary incontinence in a subject, the method comprising administering to a subject in need thereof, a non-occlusive topical or transdermal composition according to claim 8.

11. The method of claim 10, wherein the oxybutynin is in the form of its free base or as a pharmaceutically acceptable salt selected from the group consisting of acetate, bitartrate, citrate, edetate, edisylate, estolate, esylate, fumarate, gluceptate, gluconate, glutamate, hydrobromide, hydrochloride, lactate, malate, maleate, mandelate, mesylate, methylnitrate, mucate, napsylate, nitrate, pamoate, pantothenate, phosphate, salicylate, stearate, succinate, sulfate, tannate and tartrate.

12. The method of claim 11, wherein the method reduces peak plasma concentrations of oxybutynin, and further wherein the method lowers a number of incidences or lowers intensities of oxybutynin-associated side effects.

13. The method of claim 11, wherein the oxybutynin is in the form of its free base and the method provides a steady plasma oxybutynin concentration.

14. The method of claim 11, wherein the daily dosage of oxybutynin is about 30 to 60 milligrams over a 24-hour period, and further wherein composition is in the form of a gel.

15. The method of clam 10, wherein the oxybutynin is recemate and further wherein the subject is dosed with about 1 to about 20 mg over a 24-hour period.

16. The method of claim 10, wherein the oxybutynin is an enantiomer, and further wherein the subject is dosed with about 0.5 to about 15 mg over a 24-hour period.

17. The method of claim 10, wherein the composition further comprises a gelling agent, solvent, antimicrobial agent, preservative, antioxidant, buffer, humectant, sequestering agent, moisturizer, emollient, or additional permeation enhancer.

18. The method of claim 10, wherein the composition administered to the subject is in the form of an ointment, cream, gel, foam, lotion, liposome, micelle, microsphere, lacquer, patch, bandage, occlusive or non occlusive dressing or a combination thereof 19. A non-occlusive gel composition for topical or transdermal administration of oxybutynin, consisting essentially of:
  oxybutynin, oxybutynin free base or a pharmaceutically acceptable salt of oxybutynin present in an amount between about 1 to 5% by weight of the formulation;
  urea present in an amount of about 1 to 10% by weight of the formulation; and a carrier present in an amount of about 40 to 80 percent by weight of the formulation, wherein the carrier consists essentially of the combination of
  an alcohol selected from the group consisting of ethanol, propanol, isopropanol, 1-butanol, 2-butanol or a mixture thereof,
  a polyalcohol selected from the group consisting of propylene glycol, dipropylene glycol or a mixture thereof,
  a monoalkyl ether of diethylene glycol selected from the group consisting of diethylene glycol monomethyl ether, diethylene glycol monoethyl ether or a mixture thereof, or a tetraglycol furol, and water,
  wherein the alcohol is present in an amount of about 30 to 70 percent by weight of the formulation, the polyalcohol is present in an amount of about 1 to 15% by weight of the formulation, and the monoalkyl ether of diethylene glycol or a tetraglycol furol, whichever is included, is present in an amount of about 1 to 15% by weight of the formulation.

20. A method for treating overactive bladder or urge and urinary incontinence in a subject, the method comprising administering to a subject in need thereof, a non-occlusive topical or transdermal composition according to claim 19.

* * * * *

UNITED STATES PATENT AND TRADEMARK OFFICE
CERTIFICATE OF CORRECTION

PATENT NO. : 7,425,340 B2 Page 1 of 1
APPLICATION NO. : 11/120306
DATED : September 16, 2008
INVENTOR(S) : Grenier et al.

It is certified that error appears in the above-identified patent and that said Letters Patent is hereby corrected as shown below:

Column 39:
Line 37 (claim 8, last line), change "1500" to -- 15% --.
Line 42 (claim 9, line 5), change "thereof the" to -- thereof; the --.

Column 40:
Line 35 (claim 19, line 8), after "the formulation; and" start a new paragraph with "a carrier present".
Line 47 (claim 19, line 20), after "thereof, or a tetraglycol furol, and" start a new paragraph with "water".

Signed and Sealed this

Second Day of December, 2008

JON W. DUDAS
*Director of the United States Patent and Trademark Office*